United States Patent
Bordey et al.

(10) Patent No.: US 12,186,307 B2
(45) Date of Patent: Jan. 7, 2025

(54) METHODS OF TREATING EPILEPSY

(71) Applicant: YALE UNIVERSITY, New Haven, CT (US)

(72) Inventors: Angelique Bordey, Guilford, CT (US); Longbo Zhang, Guilford, CT (US)

(73) Assignee: Yale University, New Haven, CT (US)

(*) Notice: Subject to any disclaimer, the term of this patent is extended or adjusted under 35 U.S.C. 154(b) by 755 days.

(21) Appl. No.: 17/430,549

(22) PCT Filed: Feb. 13, 2020

(86) PCT No.: PCT/US2020/018136
§ 371 (c)(1),
(2) Date: Aug. 12, 2021

(87) PCT Pub. No.: WO2020/168096
PCT Pub. Date: Aug. 20, 2020

(65) Prior Publication Data
US 2022/0257572 A1    Aug. 18, 2022

Related U.S. Application Data

(60) Provisional application No. 62/958,947, filed on Jan. 9, 2020, provisional application No. 62/810,094, filed
(Continued)

(51) Int. Cl.
*A61K 31/438* (2006.01)
*A61K 31/192* (2006.01)
(Continued)

(52) U.S. Cl.
CPC .......... *A61K 31/438* (2013.01); *A61K 31/192* (2013.01); *A61P 25/08* (2018.01);
(Continued)

(58) Field of Classification Search
None
See application file for complete search history.

(56) References Cited

U.S. PATENT DOCUMENTS 8,580,809 B2    11/2013    Barbier et al.
8,614,324 B2    12/2013    Burns Barbier et al.
(Continued)

FOREIGN PATENT DOCUMENTS

WO    2014028755 A1    2/2014
WO    2018200411 A1    11/2018

OTHER PUBLICATIONS

Guerrini et al., Am J Med Genet. 2001 Summer;106(2):160-73 (Year: 2001).*
(Continued)

*Primary Examiner* — Jeffrey S Lundgren
*Assistant Examiner* — Anthony Joseph Seitz
(74) *Attorney, Agent, or Firm* — Saul Ewing LLP; Justin Crotty; Kathryn Doyle

(57) ABSTRACT

In various aspects and embodiments the invention provides a method of treating epilepsy in a subject in need thereof, the method comprising providing to the subject an effective amount of an FLNA modulator. In various embodiments, the FLNA modulator is PTI-125 or kartogenin. In various embodiments, the epilepsy is epilepsy associated with focal cortical dysplasia (FCD) type II or tuberous sclerosis complex (TSC).

5 Claims, 20 Drawing Sheets
Specification includes a Sequence Listing.

Related U.S. Application Data on Feb. 25, 2019, provisional application No. 62/805,792, filed on Feb. 14, 2019, provisional application No. 62/805,151, filed on Feb. 13, 2019.

(51) Int. Cl.
  *A61P 25/08* (2006.01)
  *A61P 25/28* (2006.01)
  *G01N 33/68* (2006.01)

(52) U.S. Cl.
  CPC .......... *A61P 25/28* (2018.01); *G01N 33/6896* (2013.01); *G01N 2333/4712* (2013.01); *G01N 2333/70571* (2013.01); *G01N 2800/2821* (2013.01); *G01N 2800/50* (2013.01)

(56) References Cited

U.S. PATENT DOCUMENTS

| | | | |
|---|---|---|---|
| 9,340,558 | B2 | 5/2016 | Barbier et al. |
| 9,354,223 | B2 | 5/2016 | Wang et al. |
| 2009/0036420 | A1 | 2/2009 | Galley et al. |
| 2011/0065681 | A1 | 3/2011 | Wei et al. |
| 2011/0105481 | A1* | 5/2011 | Burns Barbier ........ A61P 29/00 544/6 |
| 2014/0018341 | A1 | 1/2014 | Wang et al. |
| 2014/0094482 | A1 | 4/2014 | Thornton et al. |

OTHER PUBLICATIONS

Leventer RJ, Guerrini R, Dobyns WB. Malformations of cortical development and epilepsy. Dialogues Clin Neurosci. 2008;10(1):47-62 (Year: 2008).*

Bahremand et al., Epilepsy Research, vol. 81, Issue 1, 2008, pp. 44-51 (Year: 2008).*

Guerrini, R., Marini, C. Genetic malformations of cortical development. Exp Brain Res 173, 322-333 (2006). (Year: 2006).*

Burns, Lindsay H., et al., "PTI-609: A Novel Analgesic that Binds Filamin A to Control Opioid Signaling", Recent Patents on CNS Drug Discovery, vol. 5, Nov. 2010, 210-220.

Hazrati, Lili-Naz, et al., "Astrocytic Inclusions in Epilepsy: Expanding the Spectrum of Filaminopathies", Neuropathol. Exp. Neurol., Jul. 2008, 669-676.

Hsieh, Lawrence S., et al., "Convulsive seizures from experimental focal cortical dysplasia occur independently of cell misplacement", Nature Communications, Jun. 1, 2016, 1-12.

Hsieh, Lawrence S., et al., "Ectopic HCN4 expression drives mTOR-dependent epilepsy", http://dx.doi.org/10.1101/853820, Nov. 24, 2019, 1-36.

Johnson, Kristen, et al., "A Stem Cell-Based Approach to Cartilage Repair", Science Mag., vol. 336, May 11, 2012, 717-718.

Wang, Hoau-Yan, et al., "PTI-125 binds and reverses an altered conformation of filamin A to reduce Alzheimer's disease pathogenesis", Neurobiol. Aging, vol. 55, Jul. 2017, 99-14.

Zhang, Longbo, et al., "Filamin A inhibition reduces seizure activity in a mouse model of focal cortical malformations", Science Translation Medicine, vol. 12(531), Feb. 19, 2020, 1-6.

Zhang, Longbo, et al., "MEK-ERK1/2-Dependent FLNA Overexpression Promotes Abnormal Dendritic Patterning in Tuberous Sclerosis Independent of mTOR", Neuron Art., vol. 84, Oct. 1, 2014, 78-91.

Bordey, Angelique, "ERK-Filamin A dysregulation in mTOR-associated epilepsy", (PowerPoint Presentation), Yale School of Medicine Dept. of Neurosurgery, Dec. 2, 2016, AES Annual Meeting, 15 pages.

Bordey, Angelique, "Filamin A in TSC", Natl. Inst. of Health, Abstract, Project No. 5R01NS093704-04, Feb. 1, 2016, https://reporter.nih.gov/project-details/9625828, pp. 1-4.

* cited by examiner

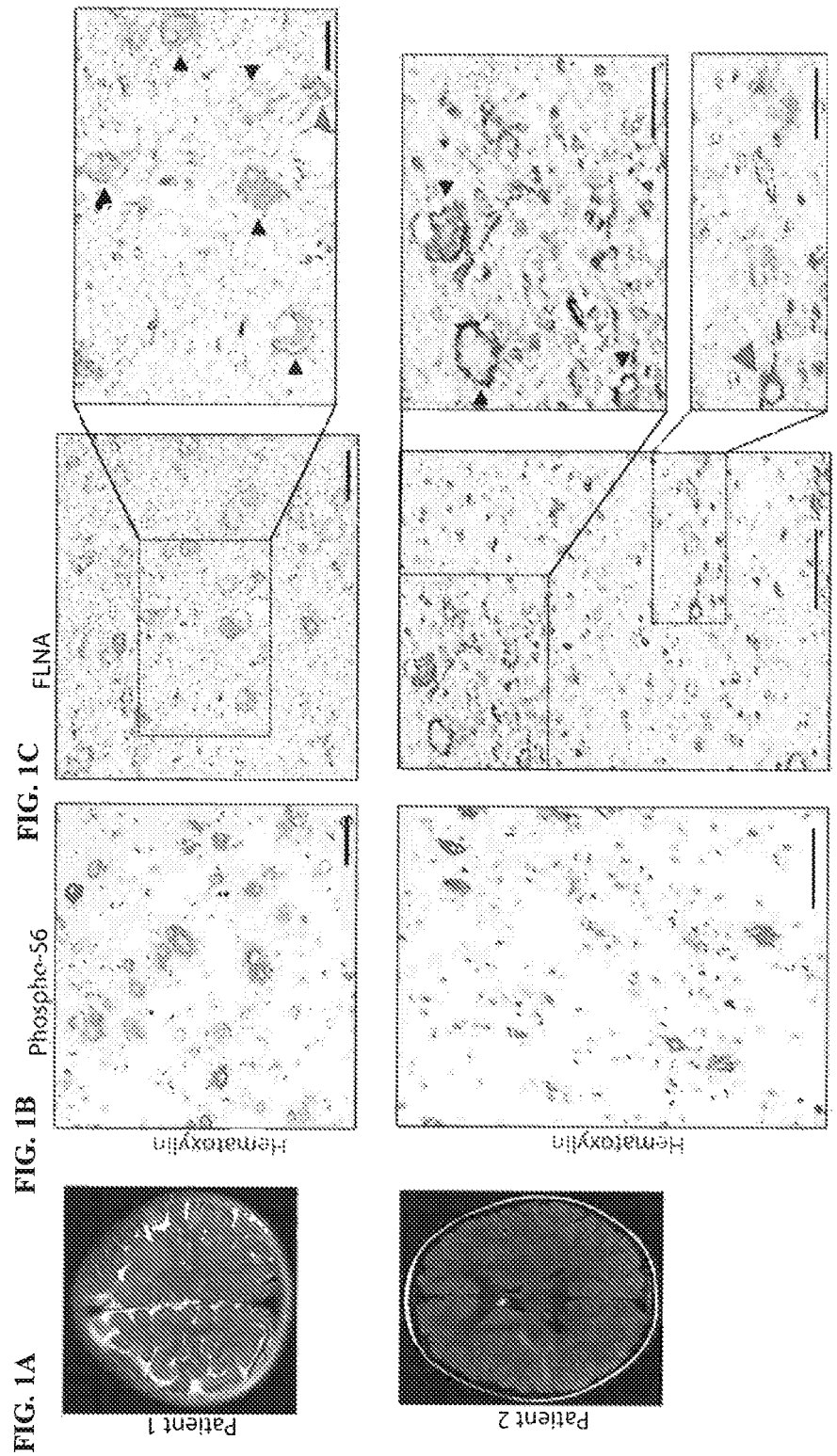

FIG. 1D 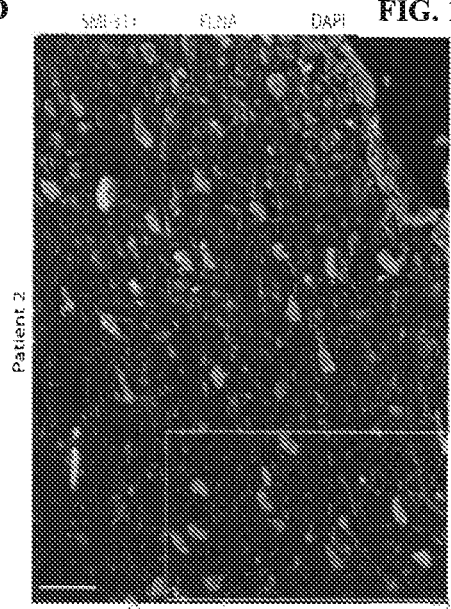 FIG. 1E 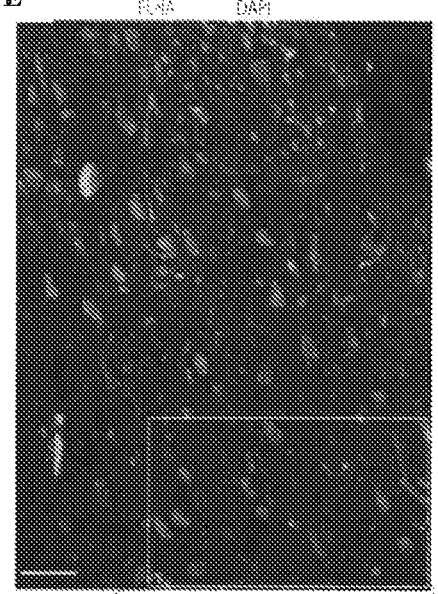
FIG. 1F 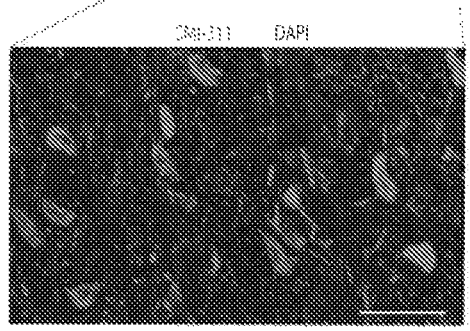 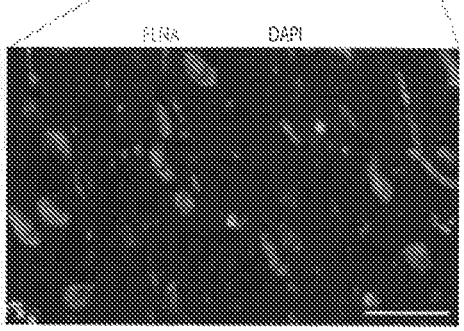
FIG. 1G 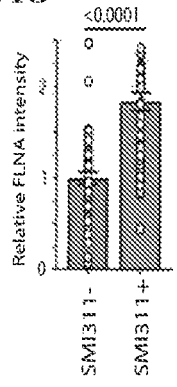 FIG. 1H 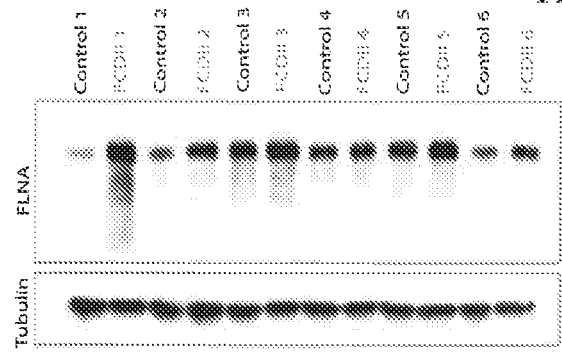 FIG. 1I 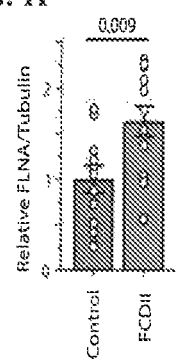

FIG. 3A
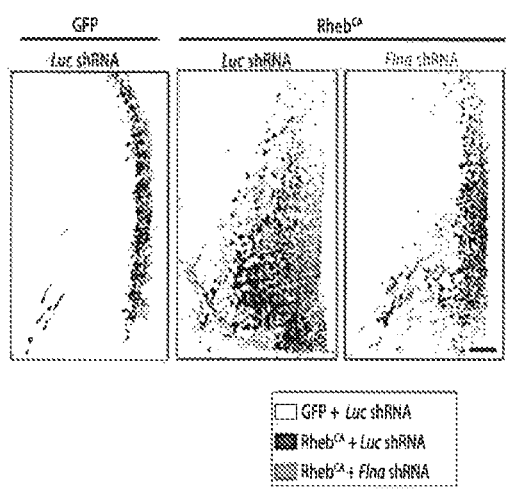
FIG. 3B
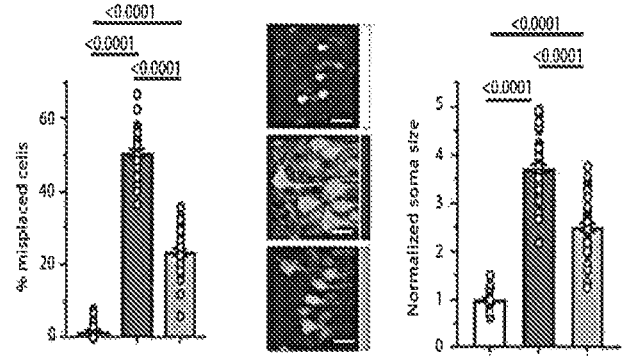
FIG. 3C
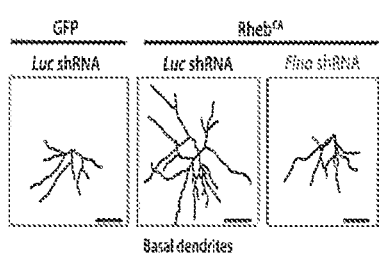
FIG. 3D
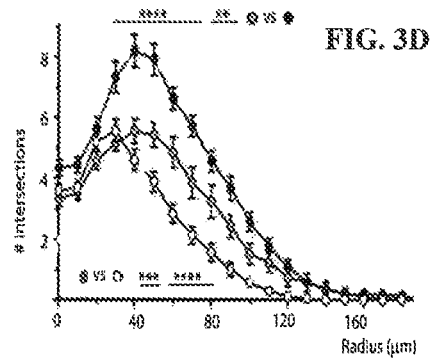
FIG. 3E
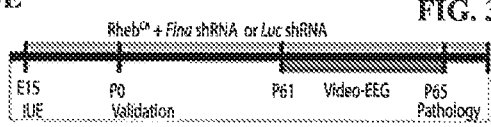
FIG. 3F
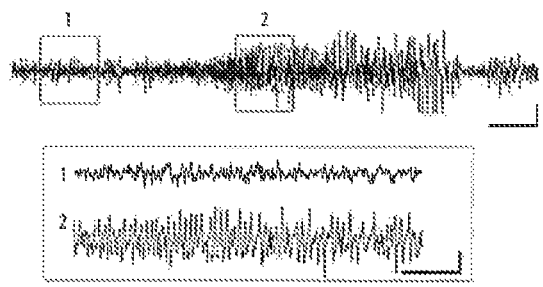
FIG. 3G
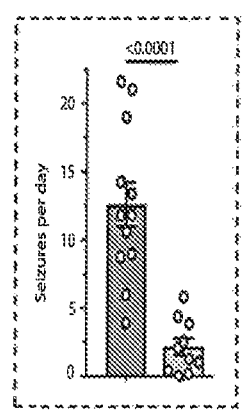
FIG. 3H
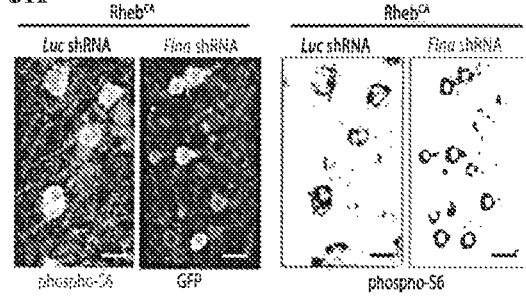
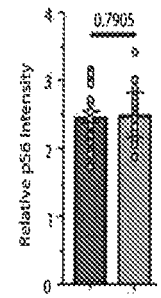

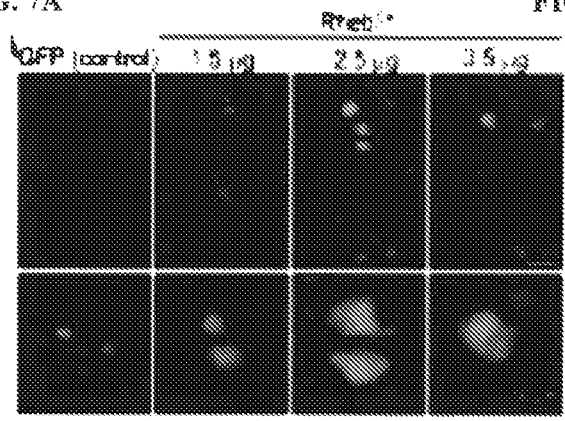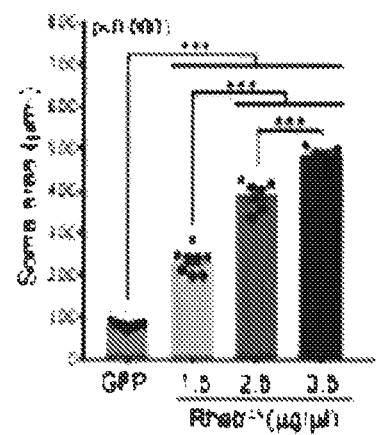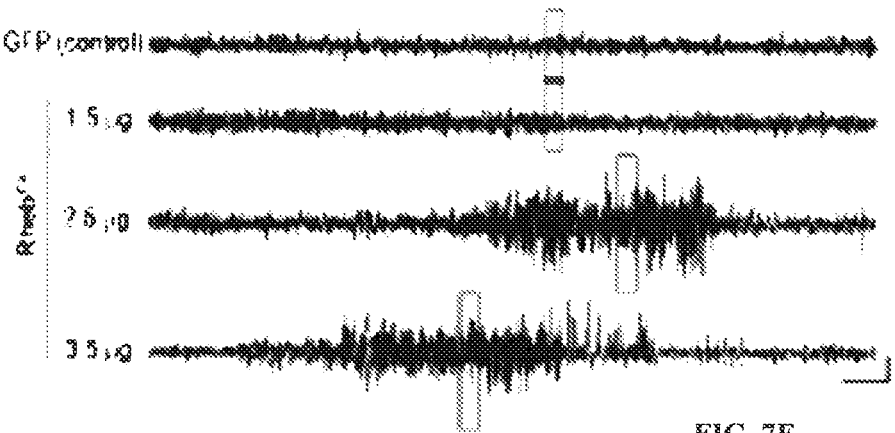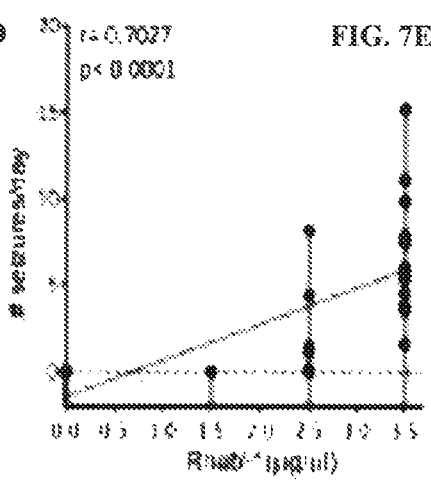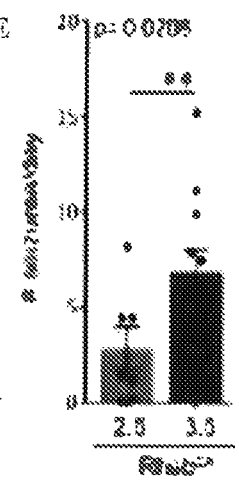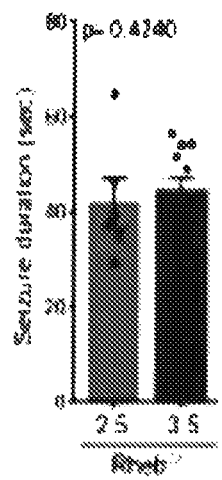

FIG. 11A
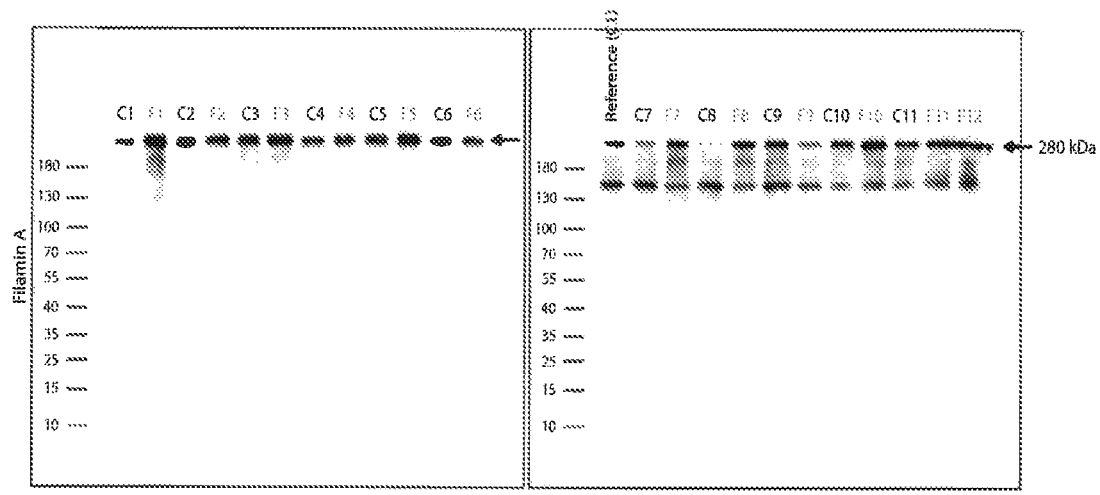
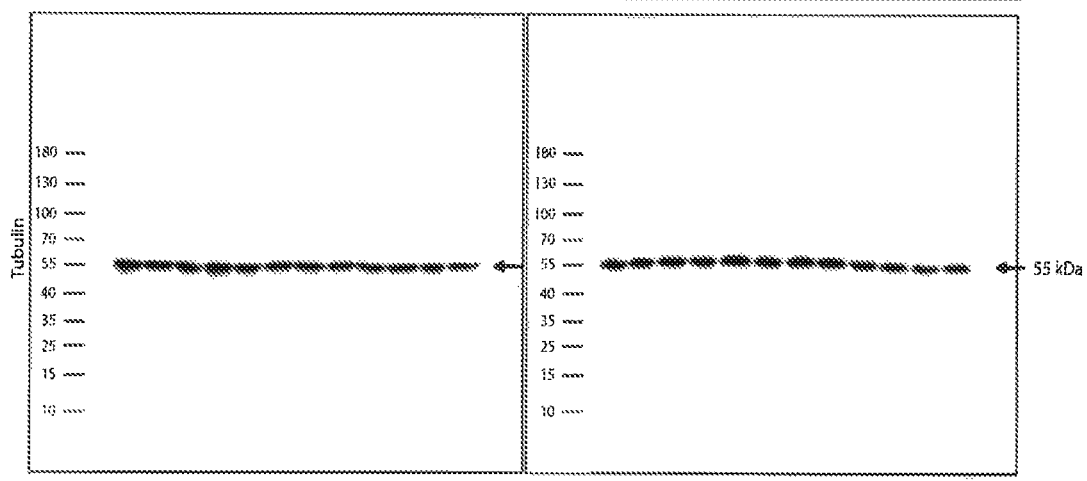
FIG. 11B

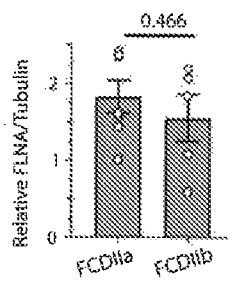
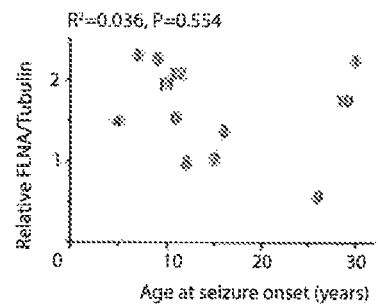
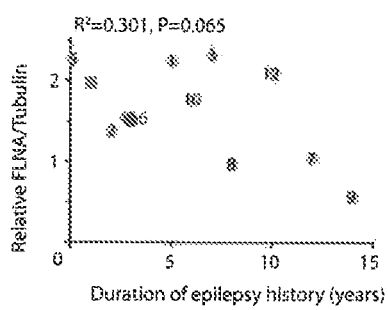
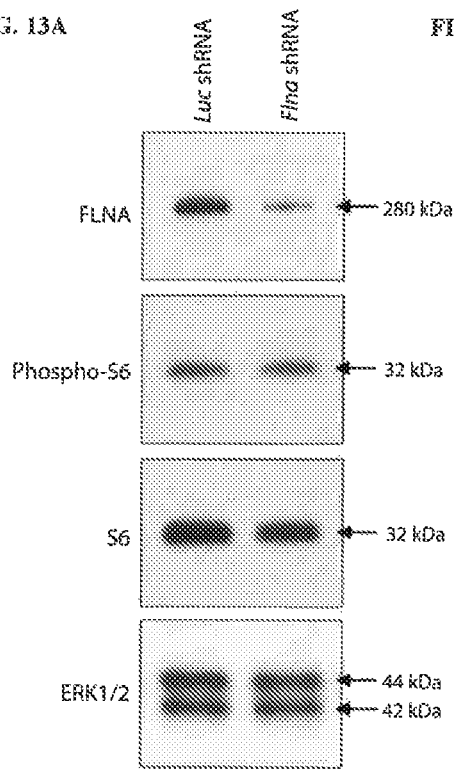
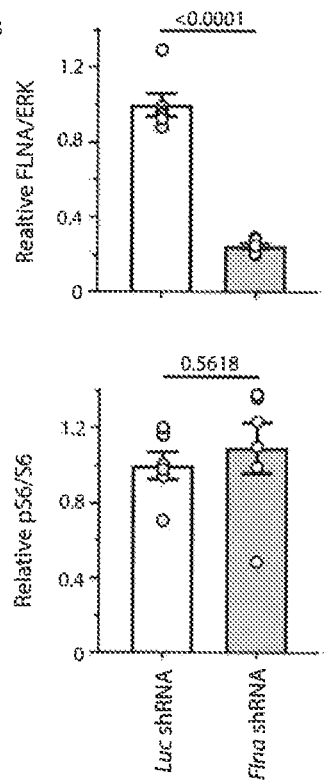

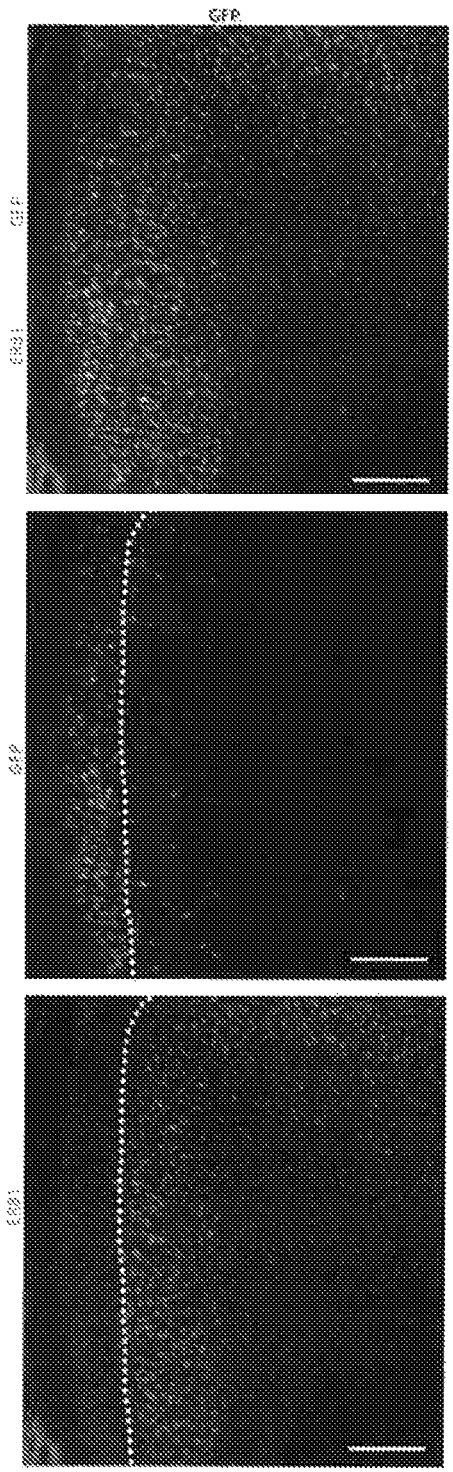 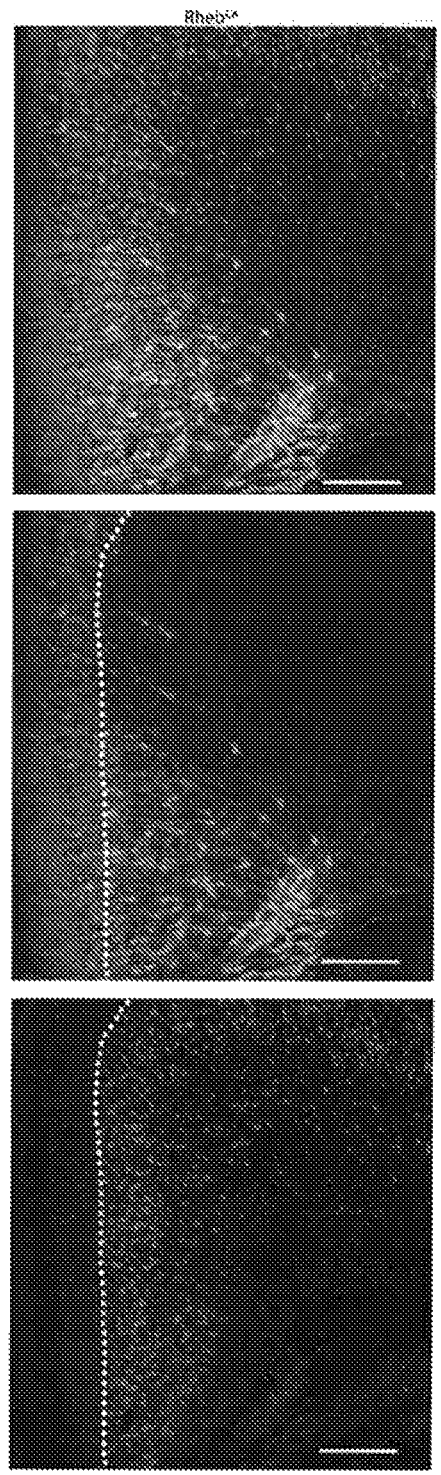
FIG. 14A
FIG. 14B

FIG. 15A
FIG. 15B
FIG. 15C
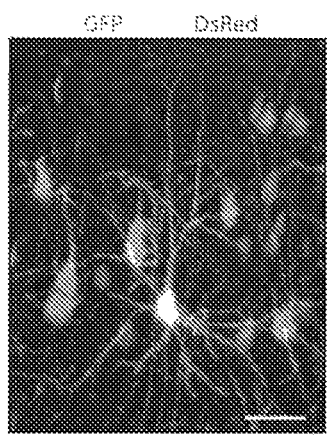
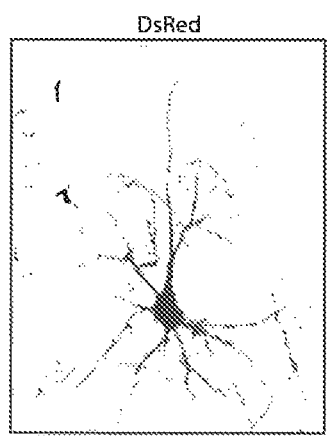
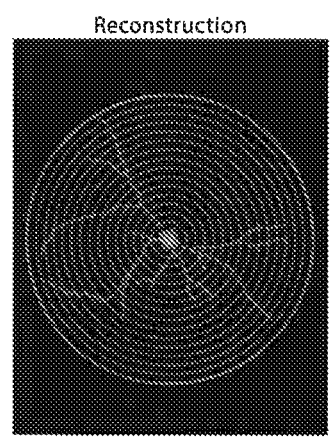

TO FIG. 16D-2

SEQUENCE LISTING

```
<160> NUMBER OF SEQ ID NOS: 1

<210> SEQ ID NO 1
<211> LENGTH: 2620
<212> TYPE: PRT
<213> ORGANISM: Homo sapiens

<400> SEQUENCE: 1

Met Pro Ala Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
                20                  25                  30

Val Ser Lys Arg Ile Ala Asn Leu Gln Thr Asp Leu Ser Asp Gly Leu
            35                  40                  45

Arg Leu Ile Ala Leu Leu Glu Val Leu Ser Gln Lys Lys Met His Arg
        50                  55                  60

Lys His Asn Gln Arg Pro Thr Phe Arg Gln Met Gln Leu Glu Asn Val
65                  70                  75                  80

Ser Val Ala Leu Glu Phe Leu Asp Arg Glu Ser Ile Lys Leu Val Ser
                85                  90                  95

Ile Asp Ser Lys Ala Ile Val Asp Gly Asn Leu Lys Leu Ile Leu Gly
                100                 105                 110
```

-continued

Leu Ile Trp Thr Leu Ile Leu His Tyr Ser Ile Ser Met Pro Met Trp
            115                 120                 125

Asp Glu Glu Asp Glu Glu Ala Lys Lys Gln Thr Pro Lys Gln Arg
    130                 135                 140

Leu Leu Gly Trp Ile Gln Asn Lys Leu Pro Gln Leu Pro Ile Thr Asn
145                 150                 155                 160

Phe Ser Arg Asp Trp Gln Ser Gly Arg Ala Leu Gly Ala Leu Val Asp
            165                 170                 175

Ser Cys Ala Pro Gly Leu Cys Pro Asp Trp Asp Ser Trp Asp Ala Ser
            180                 185                 190

Lys Pro Val Thr Asn Ala Arg Glu Ala Met Gln Gln Ala Asp Asp Trp
            195                 200                 205

Leu Gly Ile Pro Gln Val Ile Thr Pro Glu Glu Ile Val Asp Pro Asn
210                 215                 220

Val Asp Glu His Ser Val Met Thr Tyr Leu Ser Gln Phe Pro Lys Ala
225                 230                 235                 240

Lys Leu Lys Pro Gly Ala Pro Leu Arg Pro Lys Leu Asn Pro Lys Lys
            245                 250                 255

Ala Arg Ala Tyr Gly Pro Gly Ile Glu Pro Thr Gly Asn Met Val Lys
            260                 265                 270

Lys Arg Ala Glu Phe Thr Val Glu Thr Arg Ser Ala Gly Gln Gly Glu
            275                 280                 285

Val Leu Val Tyr Val Glu Asp Pro Ala Gly His Gln Glu Glu Ala Lys
            290                 295                 300

Val Thr Ala Asn Asn Asp Lys Asn Arg Thr Phe Ser Val Trp Tyr Val
305                 310                 315                 320

Pro Glu Val Thr Gly Thr His Lys Val Thr Val Leu Phe Ala Gly Gln
            325                 330                 335

His Ile Ala Lys Ser Pro Phe Glu Val Tyr Val Asp Lys Ser Gln Gly
            340                 345                 350

Asp Ala Ser Lys Val Thr Ala Gln Gly Pro Gly Leu Glu Pro Ser Gly
            355                 360                 365

Asn Ile Ala Asn Lys Thr Thr Tyr Phe Glu Ile Phe Thr Ala Gly Ala
            370                 375                 380

Gly Thr Gly Glu Val Glu Val Val Ile Gln Asp Pro Met Gly Gln Lys
385                 390                 395                 400

Gly Thr Val Glu Pro Gln Leu Glu Ala Arg Gly Asp Ser Thr Tyr Arg
            405                 410                 415

Cys Ser Tyr Gln Pro Thr Met Glu Gly Val His Thr Val His Val Thr
            420                 425                 430

Phe Ala Gly Val Pro Ile Pro Arg Ser Pro Tyr Thr Val Thr Val Gly
            435                 440                 445

Gln Ala Cys Asn Pro Ser Ala Cys Arg Ala Val Gly Arg Gly Leu Gln
450                 455                 460

Pro Lys Gly Val Arg Val Lys Glu Thr Ala Asp Phe Lys Val Tyr Thr
465                 470                 475                 480

Lys Gly Ala Gly Ser Gly Glu Leu Lys Val Thr Val Lys Gly Pro Lys
            485                 490                 495

Gly Glu Glu Arg Val Lys Gln Lys Asp Leu Gly Asp Gly Val Tyr Gly
            500                 505                 510

Phe Glu Tyr Tyr Pro Met Val Pro Gly Thr Tyr Ile Val Thr Ile Thr
            515                 520                 525

-continued

```
Trp Gly Gly Gln Asn Ile Gly Arg Ser Pro Phe Glu Val Lys Val Gly
    530             535                 540
Thr Glu Cys Gly Asn Gln Lys Val Arg Ala Trp Gly Pro Gly Leu Glu
545                 550                 555                 560
Gly Gly Val Val Gly Lys Ser Ala Asp Phe Val Glu Ala Ile Gly
                565                 570                 575
Asp Asp Val Gly Thr Leu Gly Phe Ser Val Glu Gly Pro Ser Gln Ala
            580                 585                 590
Lys Ile Glu Cys Asp Asp Lys Gly Asp Gly Ser Cys Asp Val Arg Tyr
        595                 600                 605
Trp Pro Gln Glu Ala Gly Glu Tyr Ala Val His Val Leu Cys Asn Ser
    610                 615                 620
Glu Asp Ile Arg Leu Ser Pro Phe Met Ala Asp Ile Arg Asp Ala Pro
625                 630                 635                 640
Gln Asp Phe His Pro Asp Arg Val Lys Ala Arg Gly Pro Gly Leu Glu
                645                 650                 655
Lys Thr Gly Val Ala Val Asn Lys Pro Ala Glu Phe Thr Val Asp Ala
            660                 665                 670
Lys His Gly Gly Lys Ala Pro Leu Arg Val Gln Val Gln Asp Asn Glu
        675                 680                 685
Gly Cys Pro Val Glu Ala Leu Val Lys Asp Asn Gly Asn Gly Thr Tyr
    690                 695                 700
Ser Cys Ser Tyr Val Pro Arg Lys Pro Val Lys His Thr Ala Met Val
705                 710                 715                 720
Ser Trp Gly Gly Val Ser Ile Pro Asn Ser Pro Phe Arg Val Asn Val
                725                 730                 735
Gly Ala Gly Ser His Pro Asn Lys Val Lys Val Tyr Gly Pro Gly Val
            740                 745                 750
Ala Lys Thr Gly Leu Lys Ala His Glu Pro Thr Tyr Phe Thr Val Asp
        755                 760                 765
Cys Ala Glu Ala Gly Gln Gly Asp Val Ser Ile Gly Ile Lys Cys Ala
    770                 775                 780
Pro Gly Val Val Gly Pro Ala Glu Ala Asp Ile Asp Phe Asp Ile Ile
785                 790                 795                 800
Arg Asn Asp Asn Asp Thr Phe Thr Val Lys Tyr Thr Pro Arg Gly Ala
                805                 810                 815
Gly Ser Tyr Thr Ile Met Val Leu Phe Ala Asp Gln Ala Thr Pro Thr
            820                 825                 830
Ser Pro Ile Arg Val Lys Val Glu Pro Ser His Asp Ala Ser Lys Val
        835                 840                 845
Lys Ala Glu Gly Pro Gly Leu Ser Arg Thr Gly Val Glu Leu Gly Lys
    850                 855                 860
Pro Thr His Phe Thr Val Asn Ala Lys Ala Ala Gly Lys Gly Lys Leu
865                 870                 875                 880
Asp Val Gln Phe Ser Gly Leu Thr Lys Gly Asp Ala Val Arg Asp Val
                885                 890                 895
Asp Ile Ile Asp His His Asp Asn Thr Tyr Thr Val Lys Tyr Thr Pro
            900                 905                 910
Val Gln Gln Gly Pro Val Gly Val Asn Val Thr Tyr Gly Gly Asp Pro
        915                 920                 925
Ile Pro Lys Ser Pro Phe Ser Val Ala Val Ser Pro Ser Leu Asp Leu
    930                 935                 940
Ser Lys Ile Lys Val Ser Gly Leu Gly Glu Lys Val Asp Val Gly Lys
```

-continued

```
945                 950                 955                 960
Asp Gln Glu Phe Thr Val Lys Ser Lys Gly Ala Gly Gln Gly Lys
                965                 970                 975
Val Ala Ser Lys Ile Val Gly Pro Gly Ala Ala Val Pro Cys Lys
                980                 985                 990
Val Glu Pro Gly Leu Gly Ala Asp Asn Ser Val Val Arg Phe Leu Pro
                995                 1000                1005
Arg Glu Glu Gly Pro Tyr Glu Val Glu Val Thr Tyr Asp Gly Val
    1010                1015                1020
Pro Val Pro Gly Ser Pro Phe Pro Leu Glu Ala Val Ala Pro Thr
    1025                1030                1035
Lys Pro Ser Lys Val Lys Ala Phe Gly Pro Gly Leu Gln Gly Gly
    1040                1045                1050
Ser Ala Gly Ser Pro Ala Arg Phe Thr Ile Asp Thr Lys Gly Ala
    1055                1060                1065
Gly Thr Gly Gly Leu Gly Leu Thr Val Glu Gly Pro Cys Glu Ala
    1070                1075                1080
Gln Leu Glu Cys Leu Asp Asn Gly Asp Gly Thr Cys Ser Val Ser
    1085                1090                1095
Tyr Val Pro Thr Glu Pro Gly Asp Tyr Asn Ile Asn Ile Leu Phe
    1100                1105                1110
Ala Asp Thr His Ile Pro Gly Ser Pro Phe Lys Ala His Val Val
    1115                1120                1125
Pro Cys Phe Asp Ala Ser Lys Val Lys Cys Ser Gly Pro Gly Leu
    1130                1135                1140
Glu Arg Ala Thr Ala Gly Glu Val Gly Gln Phe Gln Val Asp Cys
    1145                1150                1155
Ser Ser Ala Gly Ser Ala Glu Leu Thr Ile Glu Ile Cys Ser Glu
    1160                1165                1170
Ala Gly Leu Pro Ala Glu Val Tyr Ile Gln Asp His Gly Asp Gly
    1175                1180                1185
Thr His Thr Ile Thr Tyr Ile Pro Leu Cys Pro Gly Ala Tyr Thr
    1190                1195                1200
Val Thr Ile Lys Tyr Gly Gly Gln Pro Val Pro Asn Phe Pro Ser
    1205                1210                1215
Lys Leu Gln Val Glu Pro Ala Val Asp Thr Ser Gly Val Gln Cys
    1220                1225                1230
Tyr Gly Pro Gly Ile Glu Gly Gln Gly Val Phe Arg Glu Ala Thr
    1235                1240                1245
Thr Glu Phe Ser Val Asp Ala Arg Ala Leu Thr Gln Thr Gly Gly
    1250                1255                1260
Pro His Val Lys Ala Arg Val Ala Asn Pro Ser Gly Asn Leu Thr
    1265                1270                1275
Glu Thr Tyr Val Gln Asp Arg Gly Asp Gly Met Tyr Lys Val Glu
    1280                1285                1290
Tyr Thr Pro Tyr Glu Glu Gly Leu His Ser Val Asp Val Thr Tyr
    1295                1300                1305
Asp Gly Ser Pro Val Pro Ser Pro Phe Gln Val Pro Val Thr
    1310                1315                1320
Glu Gly Cys Asp Pro Ser Arg Val Arg Val His Gly Pro Gly Ile
    1325                1330                1335
Gln Ser Gly Thr Thr Asn Lys Pro Asn Lys Phe Thr Val Glu Thr
    1340                1345                1350
```

```
Arg Gly Ala Gly Thr Gly Gly Leu Gly Leu Ala Val Glu Gly Pro
1355                1360                1365

Ser Glu Ala Lys Met Ser Cys Met Asp Asn Lys Asp Gly Ser Cys
1370                1375                1380

Ser Val Glu Tyr Ile Pro Tyr Glu Ala Gly Thr Tyr Ser Leu Asn
1385                1390                1395

Val Thr Tyr Gly Gly His Gln Val Pro Gly Ser Pro Phe Lys Val
1400                1405                1410

Pro Val His Asp Val Thr Asp Ala Ser Lys Val Lys Cys Ser Gly
1415                1420                1425

Pro Gly Leu Ser Pro Gly Met Val Arg Ala Asn Leu Pro Gln Ser
1430                1435                1440

Phe Gln Val Asp Thr Ser Lys Ala Gly Val Ala Pro Leu Gln Val
1445                1450                1455

Lys Val Gln Gly Pro Lys Gly Leu Val Glu Pro Val Asp Val Val
1460                1465                1470

Asp Asn Ala Asp Gly Thr Gln Thr Val Asn Tyr Val Pro Ser Arg
1475                1480                1485

Glu Gly Pro Tyr Ser Ile Ser Val Leu Tyr Gly Asp Glu Glu Val
1490                1495                1500

Pro Arg Ser Pro Phe Lys Val Lys Val Leu Pro Thr His Asp Ala
1505                1510                1515

Ser Lys Val Lys Ala Ser Gly Pro Gly Leu Asn Thr Thr Gly Val
1520                1525                1530

Pro Ala Ser Leu Pro Val Glu Phe Thr Ile Asp Ala Lys Asp Ala
1535                1540                1545

Gly Glu Gly Leu Leu Ala Val Gln Ile Thr Asp Pro Glu Gly Lys
1550                1555                1560

Pro Lys Lys Thr His Ile Gln Asp Asn His Asp Gly Thr Tyr Thr
1565                1570                1575

Val Ala Tyr Val Pro Asp Val Thr Gly Arg Tyr Thr Ile Leu Ile
1580                1585                1590

Lys Tyr Gly Gly Asp Glu Ile Pro Phe Ser Pro Tyr Arg Val Arg
1595                1600                1605

Ala Val Pro Thr Gly Asp Ala Ser Lys Cys Thr Val Thr Val Ser
1610                1615                1620

Ile Gly Gly His Gly Leu Gly Ala Gly Ile Gly Pro Thr Ile Gln
1625                1630                1635

Ile Gly Glu Glu Thr Val Ile Thr Val Asp Thr Lys Ala Ala Gly
1640                1645                1650

Lys Gly Lys Val Thr Cys Thr Val Cys Thr Pro Asp Gly Ser Glu
1655                1660                1665

Val Asp Val Asp Val Val Glu Asn Glu Asp Gly Thr Phe Asp Ile
1670                1675                1680

Phe Tyr Thr Ala Pro Gln Pro Gly Lys Tyr Val Ile Cys Val Arg
1685                1690                1695

Phe Gly Gly Glu His Val Pro Asn Ser Pro Phe Gln Val Thr Ala
1700                1705                1710

Leu Ala Gly Asp Gln Pro Ser Val Gln Pro Pro Leu Arg Ser Gln
1715                1720                1725

Gln Leu Ala Pro Gln Tyr Thr Tyr Ala Gln Gly Gly Gln Gln Thr
1730                1735                1740
```

```
Trp Ala Pro Glu Arg Pro Leu Val Gly Val Asn Gly Leu Asp Val
    1745                1750                1755

Thr Ser Leu Arg Pro Phe Asp Leu Val Ile Pro Phe Thr Ile Lys
    1760                1765                1770

Lys Gly Glu Ile Thr Gly Glu Val Arg Met Pro Ser Gly Lys Val
    1775                1780                1785

Ala Gln Pro Thr Ile Thr Asp Asn Lys Asp Gly Thr Val Thr Val
    1790                1795                1800

Arg Tyr Ala Pro Ser Glu Ala Gly Leu His Glu Met Asp Ile Arg
    1805                1810                1815

Tyr Asp Asn Met His Ile Pro Gly Ser Pro Leu Gln Phe Tyr Val
    1820                1825                1830

Asp Tyr Val Asn Cys Gly His Val Thr Ala Tyr Gly Pro Gly Leu
    1835                1840                1845

Thr His Gly Val Val Asn Lys Pro Ala Thr Phe Thr Val Asn Thr
    1850                1855                1860

Lys Asp Ala Gly Glu Gly Gly Leu Ser Leu Ala Ile Glu Gly Pro
    1865                1870                1875

Ser Lys Ala Glu Ile Ser Cys Thr Asp Asn Gln Asp Gly Thr Cys
    1880                1885                1890

Ser Val Ser Tyr Leu Pro Val Leu Pro Gly Asp Tyr Ser Ile Leu
    1895                1900                1905

Val Lys Tyr Asn Glu Gln His Val Pro Gly Ser Pro Phe Thr Ala
    1910                1915                1920

Arg Val Thr Gly Asp Asp Ser Met Arg Met Ser His Leu Lys Val
    1925                1930                1935

Gly Ser Ala Ala Asp Ile Pro Ile Asn Ile Ser Glu Thr Asp Leu
    1940                1945                1950

Ser Leu Leu Thr Ala Thr Val Val Pro Pro Ser Gly Arg Glu Glu
    1955                1960                1965

Pro Cys Leu Leu Lys Arg Leu Arg Asn Gly His Val Gly Ile Ser
    1970                1975                1980

Phe Val Pro Lys Glu Thr Gly Glu His Leu Val His Val Lys Lys
    1985                1990                1995

Asn Gly Gln His Val Ala Ser Ser Pro Ile Pro Val Val Ile Ser
    2000                2005                2010

Gln Ser Glu Ile Gly Asp Ala Ser Arg Val Arg Val Ser Gly Gln
    2015                2020                2025

Gly Leu His Glu Gly His Thr Phe Glu Pro Ala Glu Phe Ile Ile
    2030                2035                2040

Asp Thr Arg Asp Ala Gly Tyr Gly Gly Leu Ser Leu Ser Ile Glu
    2045                2050                2055

Gly Pro Ser Lys Val Asp Ile Asn Thr Glu Asp Leu Glu Asp Gly
    2060                2065                2070

Thr Cys Arg Val Thr Tyr Cys Pro Thr Glu Pro Gly Asn Tyr Ile
    2075                2080                2085

Ile Asn Ile Lys Phe Ala Asp Gln His Val Pro Gly Ser Pro Phe
    2090                2095                2100

Ser Val Lys Val Thr Gly Glu Gly Arg Val Lys Glu Ser Ile Thr
    2105                2110                2115

Arg Arg Arg Arg Ala Pro Ser Val Ala Asn Val Gly Ser His Cys
    2120                2125                2130

Asp Leu Ser Leu Lys Ile Pro Glu Ile Ser Ile Gln Asp Met Thr
```

-continued

```
                2135                2140                2145

Ala Gln Val Thr Ser Pro Ser Gly Lys Thr His Glu Ala Glu Ile
            2150                2155                2160

Val Glu Gly Glu Asn His Thr Tyr Cys Ile Arg Phe Val Pro Ala
            2165                2170                2175

Glu Met Gly Thr His Thr Val Ser Val Lys Tyr Lys Gly Gln His
            2180                2185                2190

Val Pro Gly Ser Pro Phe Gln Phe Thr Val Gly Pro Leu Gly Glu
            2195                2200                2205

Gly Gly Ala His Lys Val Arg Ala Gly Gly Pro Gly Leu Glu Arg
            2210                2215                2220

Ala Glu Ala Gly Val Pro Ala Glu Phe Ser Ile Trp Thr Arg Glu
            2225                2230                2235

Ala Gly Ala Gly Gly Leu Ala Ile Ala Val Glu Gly Pro Ser Lys
            2240                2245                2250

Ala Glu Ile Ser Phe Glu Asp Arg Lys Asp Gly Ser Cys Gly Val
            2255                2260                2265

Ala Tyr Val Val Gln Glu Pro Gly Asp Tyr Glu Val Ser Val Lys
            2270                2275                2280

Phe Asn Glu Glu His Ile Pro Asp Ser Pro Phe Val Val Pro Val
            2285                2290                2295

Ala Ser Pro Ser Gly Asp Ala Arg Arg Leu Thr Val Ser Ser Leu
            2300                2305                2310

Gln Glu Ser Gly Leu Lys Val Asn Gln Pro Ala Ser Phe Ala Val
            2315                2320                2325

Ser Leu Asn Gly Ala Lys Gly Ala Ile Asp Ala Lys Val His Ser
            2330                2335                2340

Pro Ser Gly Ala Leu Glu Glu Cys Tyr Val Thr Glu Ile Asp Gln
            2345                2350                2355

Asp Lys Tyr Ala Val Arg Phe Ile Pro Arg Glu Asn Gly Val Tyr
            2360                2365                2370

Leu Ile Asp Val Lys Phe Asn Gly Thr His Ile Pro Gly Ser Pro
            2375                2380                2385

Phe Lys Ile Arg Val Gly Glu Pro Gly His Gly Gly Asp Pro Gly
            2390                2395                2400

Leu Val Ser Ala Tyr Gly Ala Gly Leu Glu Gly Gly Val Thr Gly
            2405                2410                2415

Asn Pro Ala Glu Phe Val Val Asn Thr Ser Asn Ala Gly Ala Gly
            2420                2425                2430

Ala Leu Ser Val Thr Ile Asp Gly Pro Ser Lys Val Lys Met Asp
            2435                2440                2445

Cys Gln Glu Cys Pro Glu Gly Tyr Arg Val Thr Tyr Thr Pro Met
            2450                2455                2460

Ala Pro Gly Ser Tyr Leu Ile Ser Ile Lys Tyr Gly Gly Pro Tyr
            2465                2470                2475

His Ile Gly Gly Ser Pro Phe Lys Ala Lys Val Thr Gly Pro Arg
            2480                2485                2490

Leu Val Ser Asn His Ser Leu His Glu Thr Ser Ser Val Phe Val
            2495                2500                2505

Asp Ser Leu Thr Lys Ala Thr Cys Ala Pro Gln His Gly Ala Pro
            2510                2515                2520

Gly Pro Gly Pro Ala Asp Ala Ser Lys Val Val Ala Lys Gly Leu
            2525                2530                2535
```

-continued

```
Gly Leu Ser Lys Ala Tyr Val Gly Gln Lys Ser Ser Phe Thr Val
    2540            2545            2550

Asp Cys Ser Lys Ala Gly Asn Asn Met Leu Leu Val Gly Val His
    2555            2560            2565

Gly Pro Arg Thr Pro Cys Glu Glu Ile Leu Val Lys His Val Gly
    2570            2575            2580

Ser Arg Leu Tyr Ser Val Ser Tyr Leu Leu Lys Asp Lys Gly Glu
    2585            2590            2595

Tyr Thr Leu Val Val Lys Trp Gly Asp Glu His Ile Pro Gly Ser
    2600            2605            2610

Pro Tyr Arg Val Val Val Pro
    2615            2620
```

METHODS OF TREATING EPILEPSY

CROSS-REFERENCE TO RELATED APPLICATIONS

The present application is a 35 U.S.C. § 371 national phase application from, which claims priority to, International Application No. PCT/US2020/018136 filed Feb. 13, 2020, which claims priority under 35 U.S.C. § 119(e) to U.S. Provisional Patent Application Nos. 62/805,151 filed filed Feb. 13, 2019, 62/805,792 filed Feb. 14, 2019, 62/810,094 filed Feb. 25, 2019, and 62/958,947, filed Jan. 9, 2020, all of which are incorporated herein by reference in their entirety.

STATEMENT REGARDING FEDERALLY SPONSORED RESEARCH OR DEVELOPMENT

This invention was made with government support under NS111074 and NS093704 awarded by the National Institutes of Health. The government has certain rights in the invention.

SEQUENCE LISTING

The ASCII text file named "047162-7218US1_Sequence_ Listing_ST25" created on Aug. 12, 2021, comprising 22.9 Kbytes, is hereby incorporated by reference in its entirety.

BACKGROUND OF THE INVENTION

Epilepsy occurs in 80-90% of individuals with cortical malformations and is often refractory to treatments. The largest subset of cortical malformations shares similar molecular, histopathological, and clinical features, suggesting a common mechanism through which they contribute to epileptogenesis. These are focal cortical dysplasia (FCD) type II, STRADalpha deficiency, and tuberous sclerosis complex (TSC). Somatic mutations in these neurodevelopmental disorders occur during embryonic life and lead to hyperactivity of the mTOR complex 1 (mTORC1) and the formation of focal cortical malformations. Treatment options are limited to surgical resection of the focal cortical malformations or treatment with everolimus. Most patients will try every other drug available, but without success. Many patients cannot undergo surgery because the malformation(s) are not accessible or too numerous. In addition, surgery is an invasive and traumatic experience for patients and is not always fully successful as 30-40% of the patients will not properly manage their seizures post-surgery. Everolimus clinical trial reported that everolimus (at the highest dose) was efficient at reducing seizure frequency in a subset of patients (40%), but had side-effects and 60% of the patients saw no improvements. There is thus a critical need to find a better treatment option to reduce or eliminate their seizures in individuals with TSC or FCDII. In addition, recurrent seizures are accompanied by significant comorbidity, including neurocognitive and psychological deficits as well as poor quality of life. Preventing seizures from occurring or reducing their frequency would significantly improve the life of individuals with the disease as well as that of their caregiver. There is a need in the art for novel methods for treating epilepsy. This disclosure addresses that need.

SUMMARY OF THE INVENTION

In one aspect, the invention provides a method of treating epilepsy in a subject in need thereof, the method comprising providing to the subject an effective amount of an FLNA modulator.

In another aspect, the invention provides a method of treating focal cortical dysplasia (FCD) type II or tuberous sclerosis complex (TSC) in a subject in need thereof, the method comprising providing to the subject an effective amount of PTI-125.

In yet another aspect, the invention provides of a method of inhibiting hyperphosphorylation of the tau protein that comprises the steps of administering to cells of the central nervous system in recognized need a FLNA-binding effective amount of kartogenin or a pharmaceutically acceptable salt.

In yet another aspect, the invention provides a method for determining the likelihood of a living patient having Alzheimer's disease pathology (AD pathology) comprising the steps of
a) determining the amount of one or more of a protein-protein complex selected from the group consisting of i) α7nAChR/FLNA, ii) TLR4/FLNA and iii) α7nAChR/Aβ present in a first portion of a lymphocyte preparation from said living patient;
b) determining the amount of said one or more of i) α7nAChR/FLNA, ii) TLR4/FLNA and iii) α7nAChR/Aβ present as a protein-protein complex in a second portion of said lymphocyte preparation, said second portion of said lymphocyte portion further containing admixed therein a FLNA binding-effective amount of kartogenin or a pharmaceutically acceptable salt thereof; and
c) comparing the values so determined, whereby a determined amount of said one or more of i) α7nAChR/FLNA, ii) TLR4/FLNA and iii) α7nAChR/Aβ present as a protein-protein complex in a second portion of said lymphocyte preparation that is significantly decreased in the presence of kartogenin or pharmaceutically acceptable salt thereof indicates that the patient had AD pathology at the time the body sample was taken, whereas no significant difference between the two determined values indicates that the patient was free of AD pathology at the time the body sample was taken.

In certain embodiments, the FLNA modulator is PTI-125.
In certain embodiments, the FLNA modulator is kartogenin
In certain embodiments, the epilepsy is intractable epilepsy.
In certain embodiments, the epilepsy is associated with focal cortical dysplasia (FCD) type II or tuberous sclerosis complex (TSC) or hemimegalencephaly.
In certain embodiments, the FLNA modulator is formulated in a pharmaceutical composition comprising at least one pharmaceutically acceptable excipient.
In certain embodiments, the subject is a mammal. In certain embodiments, the subject is a human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A-H depict that FLNA expression is increased in cortices of patients with FCDII. (FIG. 1A) MRI scans of a 2-year and a 5-year old patient with FCDII with seizures. The arrow points to the FCM. (FIG. 1B and FIG. 1C) Images of phospho-S6 (FIG. 1B) and FLNA (FIG. 1C) staining in hematoxylin-stained sections from the FCM in the brain of patients whose scans are shown in (FIG. 1A). Arrows point to FLNA-positive balloon cells and dysmorphic neurons. (FIG. 1D and FIG. 1E) Co-immunostaining for FLNA and a marker of cytomegalic neurons, SMI-311 and DAPI counterstain in human FCDII tissue. (FIG. 1F) Magnification of SMI311 or FLNA staining with DAPI from images in the white square in FIG. 1D and FIG. 1E. (FIG. 1G) Quantification of FLNA staining in SMI-311-positive neurons relative to surrounding SMI-311-negative cells. Only SMI-311-negative cells with visible FLNA staining (to outline the cell body) were used for quantification. (FIG. 1H and FIG. 1I) Immunoblots of FLNA and tubulin from resected FCDII tissue (FIG. 1H) and quantification from 12 patients with FCDII(I). The numbers correspond to those of the patients listed in Tables 1 and 2. FLNA and tubulin size were 280 and 55 kDa, respectively. Unpaired Student t-test. Data are mean±SEM. n number are listed in Table 3. Scale bars: 100 µm.

(FIG. 2A) FLNA (280 kDa), pS6 (32 kDa), S6 (32 kDa), and GAPDH (37 kDa) immunoblots in cultured neurons expressing plasmids encoding GFP, mTORC1 mutants, or $Rheb^{CA}$. (FIG. 2B and FIG. 2C) Quantification of the blots show in FIG. 1A. (FIG. 2D) Diagram of the experimental procedure for generating FCM in mice followed by video-EEG recordings and immunoblotting or immunochemistry. (FIG. 2E and FIG. 2F) FLNA immunostaining in sections from mouse FCM (FIG. 2E) and quantification in GFP-positive $Rheb^{CA}$-expressing cells relative to surrounding GFP-negative cells (FIG. 2F). Scale bar: 100 µm. (FIG. 2G) FLNA and GAPDH immunoblots. Ipsi: ipsilateral and Contra: contralateral. (FIG. 2H) FLNA/GAPDH quantification in FCM-containing cortices relative to contralateral cortices in mice electroporated with $Rheb^{CA}$. One way ANOVA (FIG. 2B and FIG. 2C), unpaired and paired Student t-test (FIG. 2F and FIG. 2H, respectively). Data are mean±SEM. N number are listed in Table 3.

FIG. 3A-3H depict that normalizing the amount of FLNA in dysmorphic neurons of mTORC1-driven FCM partially prevents cytoarchitectural abnormalities and attenuates seizure activity. (FIG. 3A) Images of control or $Rheb^{CA}$-expressing neurons co-expressing luciferase or Flna shRNA in littermate mice, and quantification of neuronal placement in the different conditions. Scale bar: 250 µm. (FIG. 3B) Images of GFP+ electroporated neurons in different conditions and quantification of soma size. Scale bar: 50 µm. (FIG. 3C) Basal dendrite reconstruction and corresponding Sholl analysis. Scale bar: 50 µm. (FIG. 3D) Bar graphs of the basal total dendrite length (TDL). (FIG. 3E) Diagram of the experimental procedure. (FIG. 3F) Representative EEG traces in a control shRNA seizing mouse. Scales: 200 µV/5 s and 1 s (inset). (FIG. 3G) Frequency of seizures in the Luc or Flna shRNA condition. (FIG. 3H) Phospho-S6 immunostaining and quantification in GFP+ $Rheb^{CA}$-expressing neurons (normalized to surrounding GFP-neurons) in EEG-recorded mice. Scale bar: 50 µm. Mann Whitney tests (FIG. 3G), one-way ANOVA (FIGS. 3A, 3B, and 3D) and two-way repeated measure ANOVA (FIG. 3C), and Student's t test (FIG. 3H). Data are mean±SEM. N number are listed in Table 3.

(FIG. 4A) Diagram of experimental paradigm. (FIG. 4B) Images of neuronal soma following treatment with vehicle or different PTI-125 doses and quantification. Scale bar: 50 µm. (FIG. 4C and FIG. 4D) Reconstructions of basal dendrites (FIG. 4C), Sholl analyses, and basal total dendritic length (TDL, FIG. 4D) under different treatment conditions. (FIG. 4E) Immunoblots of phospho-S6 (pS6), S6 and GAPDH from the cortices of mice treated with vehicle (saline) or PTI-125, and quantification. (FIG. 4F) Diagram of experimental paradigm. (FIG. 4G) Seizure frequency (6 day-long recordings) following vehicle or PTI-125 treatment at 12 mg/kg. (FIG. 4H) Plots of the weight gain during vehicle or PTI-125 treatment from P8-P60. Inset: mean body weight between P52-P60. (FIG. 4I) Quantification of cell misplacement in mice treated with vehicle or PTI-125. (FIG. 4J) Images of phoshpo-S6 (pS6) immunostaining and GFP fluorescence in coronal sections containing $Rheb^{CA}$-expressing cells (GFP+) and corresponding phospho-S6 (pS6) quantification normalized to the vehicle treated condition. Scale bar: 50 µm. Student t-test (FIG. 4E, FIG. 4H, FIG. 4I, and FIG. 4J), two-way repeated measure ANOVA (FIG. 4D), Mann Whitney test (FIG. 4G), and one-way ANOVA (FIG. 4B and FIG. 4D). Data are mean±SEM. N number are listed in Table 3.

(FIG. 5A) Diagram of experimental paradigm. (FIGS. 5B and 5C) Images of control GFP+ neurons and GFP+ $Rheb^{CA}$-expressing neurons in mice treated with vehicle (saline) or PTI-125 (FIG. 5b) and quantification of soma sizes (FIG. 5C). Scale bar: 120 µm. (FIG. 5D and FIG. 5E) Sholl analyses and total basal dendritic length (TDL). (FIG. 5F) Heatmap of seizure activity over time (per day) per mouse either treated with vehicle (saline) or PTI-125. (FIG. 5G) Seizure frequency following and during vehicle or PTI-125 treatment from P29 to P54. (FIG. 5H) Diagram of experimental paradigm. (FIG. 5I) Heatmap of seizure activity per individual mouse over time. In the upper heatmap, mice received vehicle injections and were recorded from P61 to P92. In the bottom heatmap, mice received vehicle from P61 to P72 and then PTI-125 until P106. For mice #5, the wires were unplugged for two days leading to loss of recordings that are colored white on the heatmap. (FIG. 5J) Bar graph of the seizure frequency at days (FIG. 5D) 1-5 and D27-31 of recordings (corresponding to P61-65 and P88-92) under continuous vehicle treatment or vehicle-to-PTI-125 treatment. (FIG. 5K) Plots of the seizure frequency prior to and after PTI-125 treatments. One-way ANOVA (FIG. 5C, FIG. 5E, and FIG. 5J), two-way repeated measure ANOVA (FIG. 5D), Mann Whitney tests (FIG. 5G), and Wilcoxon matched pairs test (FIG. 5K). Data are mean±SEM. N number are listed in Table 3.

(FIG. 6A) Percentage (%) of seizure-free mice in both conditions. Two mice in vehicle treated condition died of seizures during EEG recordings and were thus not included in FIG. 6B. (FIG. 6B and FIG. 6C) Heatmap of seizure frequency for all conditions (FIG. 6B) and corresponding scatter plot (FIG.

Figure 6A:
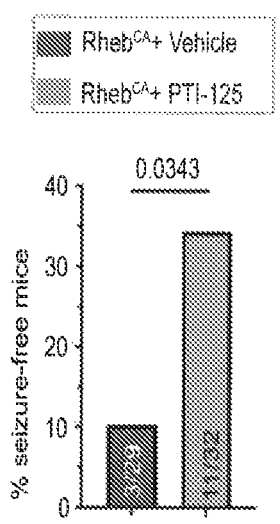
FIGS. 6A-6C depict that PTI-125 decreases the percentage of seizing mice and seizure frequency.
Figure 6B:
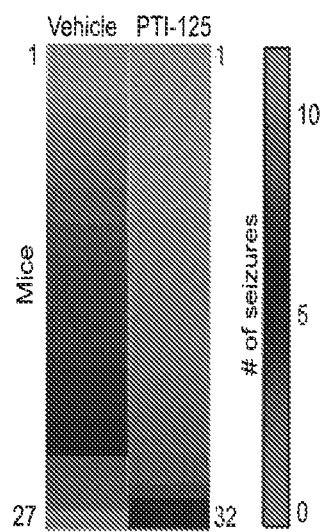
Figure 6C:
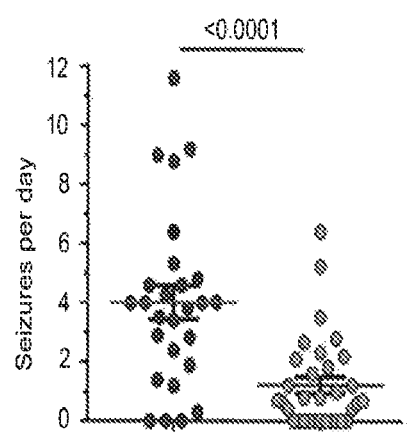

6C). Fisher Exact test (FIG. 6A) and Mann Whitney test (FIG. 6C). Data are mean±SEM.

FIG. 7A-7F depict images of GFP+ neurons in coronal sections from mice electroporated with increasing concentrations of RhebCA. FIG. 7B depicts plots of the somata size as a function of RhebCA concentration. FIG. 7C depicts representative EEG recording of seizures in the different RhebCA condition. FIG. 7D depicts a plot of the seizure frequency (#seizures per day) as a function of the concentration of RhebCA. FIGS. 7E and 7F depict plots of the seizure frequency (FIG. 7E) and duration (FIG. 7F) for two RhebCA concentrations. t-test.

Figure 8:
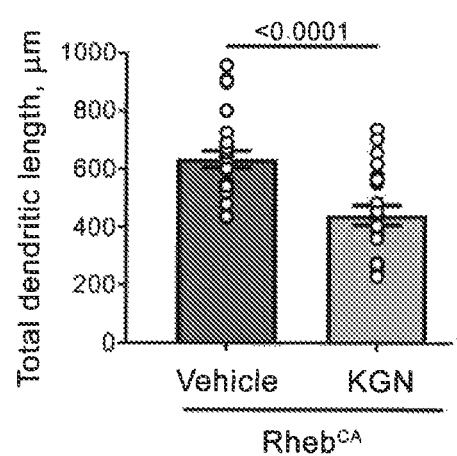
Figure 9A:
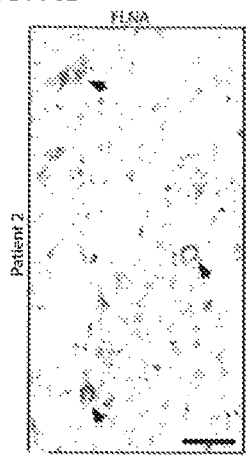
Figure 9B:
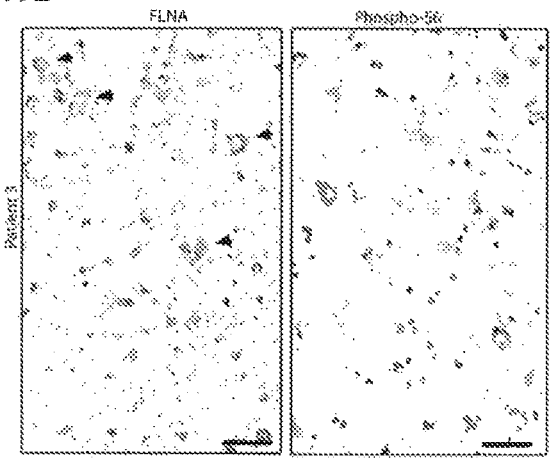
Figure 9C:
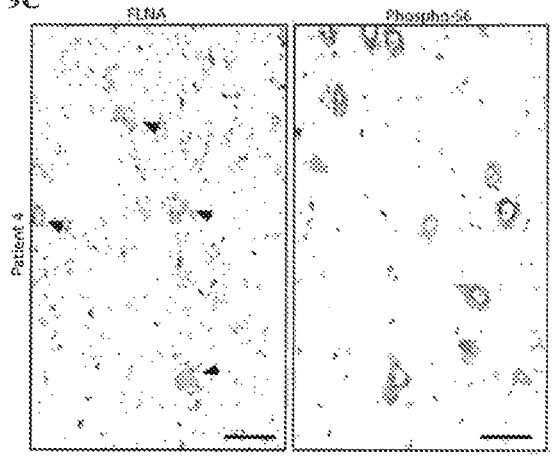
Figure 9D:
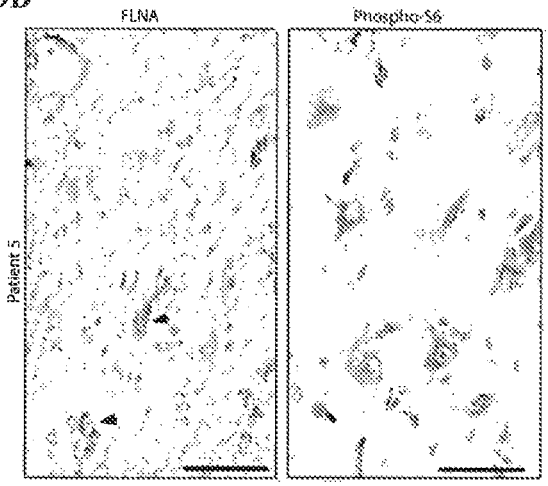
Figure 9E:
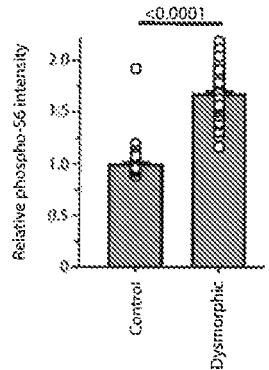
Figure 9F:
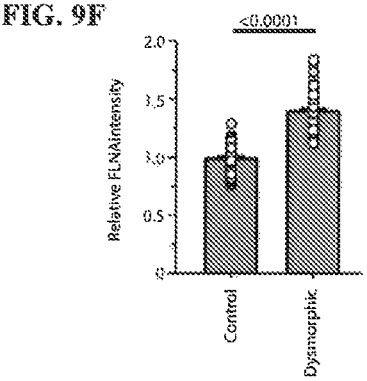

FIG. 8 depicts a graph quantifying the effect of kartogenin (KGN) or vehicle on the total neurite length in $Rheb^{CA}$-expressing neurons cultured for 7 days in vitro (DIV). Unpaired, two-sided t-test P<0.0001. Neurons were treated at the time of plating until harvesting with 5 µM KGN.

FIGS. 9A-9F depict that FLNA expression is increased in cortices of patients with FCDII. (FIG. 9A-FIG. 9D) Images of FLNA and phospho-S6 staining in hematoxylin-stained cortical sections from patients with FCDII. Scale bar: 100 µm. (FIG. 9E and FIG. 9F) Quantification of phospho-S6 and FLNA staining intensity in dysmorphic cells versus surrounding cells. Unpaired Mann-Whitney and Student t-test. Data are mean±SEM. n numbers are listed in Table 3.

Figure 10A:
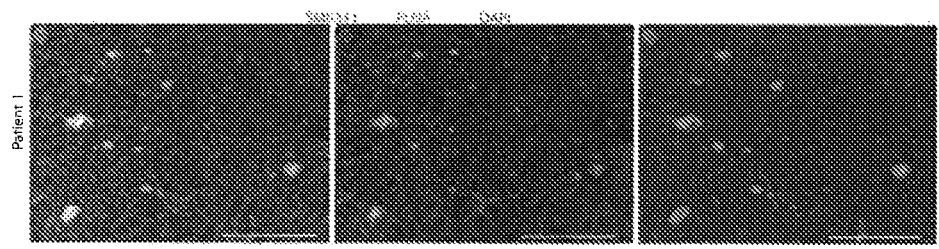
Figure 10B:
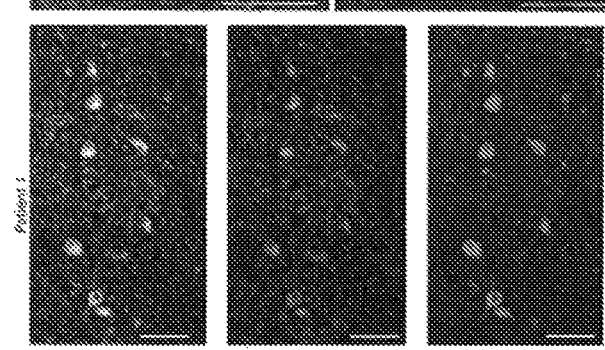
Figure 10C:
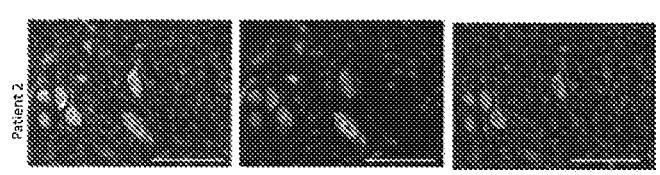
Figure 10D:
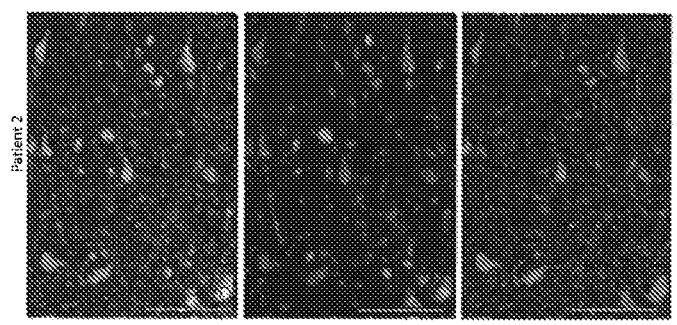
Figure 10E:
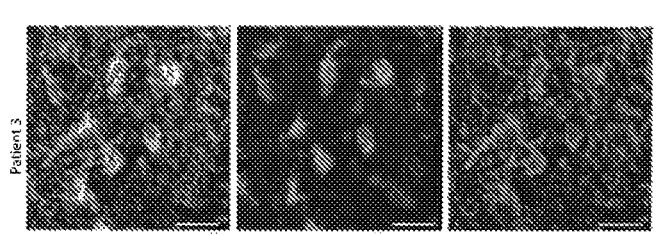

FIGS. 10A-10E depict that FLNA expression is increased in cytomegalic cortical neurons of patients with FCDII. (FIG. 10A-FIG. 10E) Images of FLNA and SMI-311 co-staining and DAPI counterstain in cortical sections from patients with FCDII. Scale bars: 140 µm (FIG. 10A, FIG. 10B, and FIG. 10D), 25 µm (FIG. 10C), and 100 µm (FIG. 10E).

FIGS. 11A-11B depict original immunoblots for FLNA in human FCDII samples. (FIG. 11A and FIG. 11B) Filamin A (FIG. 11A) and Tubulin (FIG. 11B) immunoblots on the same membranes from human FCDII (noted F) and control (noted C) cortical tissue. The ladder (from Fisher Scientific, #26617) is shown on the left of the blots. The numbers correspond to those in Tables 1 and 2 (human samples).

FIGS. 12A-12C depict that the quantity of FLNA is not correlated to the type of FCDII or age of seizure onset or epilepsy duration. (FIG. 12A) Bar graphs of FLNA quantity in FCDIIa and FCDIIb. (FIG. 12B and FIG. 12C) Scatter plots of the relative quantity of FLNA (mean control is 1) versus the age of seizure onset (FIG. 12B) or the duration of epilepsy history (FIG. 12C). The numbers correspond to the patient number listed in Table 1.

FIGS. 13A-13B depict that knocking down FLNA does not affect the degree of S6 phosphorylation. (FIG. 13A) Immunoblots for the proteins listed on the left in Neuro2A cells transfected with either luciferase or FLNA shRNA. (FIG. 13B) Quantification of FLNA/ERK and pS6/S6 quantities in both transfection conditions. Student t-test. Data are mean±SEM.

FIGS. 14A-14B depict that delineation of layer 2/3 and layer 5 neurons using ER81 immunostaining. (FIG. 14A and FIG. 14B) Immunostaining for ER81 (pseudo-colored red), a marker of layer 5 neurons, and GFP fluorescence in the anterior cingulate cortex from mice electroporated with GFP (+tdTomato) (FIG. 14A) or GFP+ $Rheb^{CA}$ (FIG. 14B) at E15. The dotted line delineates the boundary between layer 2/3 and layer 5.

FIGS. 15A-15C depict single cell labeling for dendrite (sholl) analysis. (FIG. 15A) GFP and DsRed fluorescence from pCAG-GFP and pCALNL-DsRed (inducible vector) and pCAG-Cre. (FIG. 15B) DsRed fluorescence in black and white. (FIG. 15C) Image of Sholl reconstruction of the basal dendrites of the neurons shown in FIG. 15B.

FIGS. 16A-16D depict the original immunoblots. The ladder (from Fisher Scientific, #10748010) is shown on the left of each blot.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, subcutaneous, oral, aerosol, parenteral, ophthalmic, pulmonary and topical administration.

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

As used herein, "filamin A" or "FLNA" refers to the protein for which the human homolog has the amino acid sequence:

```
                                          SEQ ID NO: 1
        10         20         30         40
  MPATEKDLAE DAPWKKIQQN TFTRWCNEHL KCVSKRIANL 50         60         70         80
  QTDLSDGLRL IALLEVLSQK KMHRKHNQRP TFRQMQLENV 90        100        110        120
  SVALEFLDRE SIKLVSIDSK AIVDGNLKLI LGLIWTLILH 130        140        150        160
  YSISMPMWDE EEDEEAKKQT PKQRLLGWIQ NKLPQLPITN
```

-continued

```
        170         180         190         200
FSRDWQSGRA  LGALVDSCAP  GLCPDWDSWD  ASKPVTNARE 210         220         230         240
AMQQADDWLG  IPQVITPEEI  VDPNVDEHSV  MTYLSQFPKA 250         260         270         280
KLKPGAPLRP  KLNPKKARAY  GPGIEPTGNM  VKKRAEFTVE 290         300         310         320
TRSAGQGEVL  VYVEDPAGHQ  EEAKVTANND  KNRTFSVWYV 330         340         350         360
PEVTGTHKVT  VLFAGQHIAK  SPFEVYVDKS  QGDASKVTAQ 370         380         390         400
GPGLEPSGNI  ANKTTYFEIF  TAGAGTGEVE  VVIQDPMGQK 410         420         430         440
GTVEPQLEAR  GDSTYRCSYQ  PTMEGVHTVH  VTFAGVPIPR 450         460         470         480
SPYTVTVGQA  CNPSACRAVG  RGLQPKGVRV  KETADFKVYT 490         500         510         520
KGAGSGELKV  TVKGPKGEER  VKQKDLGDGV  YGFEYYPMVP 530         540         550         560
GTYIVTITWG  GQNIGRSPFE  VKVGTECGNQ  KVRAWGPGLE 570         580         590         600
GGVVGKSADF  VVEAIGDDVG  TLGFSVEGPS  QAKIECDDKG 610         620         630         640
DGSCDVRYWP  QEAGEYAVHV  LCNSEDIRLS  PFMADIRDAP 650         660         670         680
QDFHPDRVKA  RGPGLEKTGV  AVNKPAEFTV  DAKHGGKAPL 690         700         710         720
RVQVQDNEGC  PVEALVKDNG  NGTYSCSYVP  RKPVKHTAMV 730         740         750         760
SWGGVSIPNS  PFRVNVGAGS  HPNKVKVYGP  GVAKTGLKAH 770         780         790         800
EPTYFTVDCA  EAGQGDVSIG  IKCAPGVVGP  AEADIDFDII 810         820         830         840
RNDNDTFTVK  YTPRGAGSYT  IMVLFADQAT  PTSPIRVKVE 850         860         870         880
PSHDASKVKA  EGPGLSRTGV  ELGKPTHFTV  NAKAAGKGKL 890         900         910         920
DVQFSGLTKG  DAVRDVDIID  HHDNTYTVKY  TPVQQGPVGV 930         940         950         960
NVTYGGDPIP  KSPFSVAVSP  SLDLSKIKVS  GLGEKVDVGK 970         980         990        1000
DQEFTVKSKG  AGGQGKVASK  IVGPSGAAVP  CKVEPGLGAD 1010        1020        1030        1040
NSVVRFLPRE  EGPYEVEVTY  DGVPVPGSPF  PLEAVAPTKP 1050        1060        1070        1080
SKVKAFGPGL  QGGSAGSPAR  FTIDTKGAGT  GGLGLTVEGP 1090        1100        1110        1120
CEAQLECLDN  GDGTCSVSYV  PTEPGDYNIN  ILFADTHIPG 1130        1140        1150        1160
SPFKAHVVPC  FDASKVKCSG  PGLERATAGE  VGQFQVDCSS 1170        1180        1190        1200
AGSAELTIEI  CSEAGLPAEV  YIQDHGDGTH  TITYIPLCPG 1210        1220        1230        1240
AYTVTIKYGG  QPVPNFPSKL  QVEPAVDTSG  VQCYGPGIEG
```

```
       1250        1260        1270        1280
QGVFREATTE  FSVDARALTQ  TGGPHVKARV  ANPSGNLTET 1290        1300        1310        1320
YVQDRGDGMY  KVEYTPYEEG  LHSVDVTYDG  SPVPSSPFQV 1330        1340        1350        1360
PVTEGCDPSR  VRVHGPGIQS  GTTNKPNKFT  VETRGAGTGG 1370        1380        1390        1400
LGLAVEGPSE  AKMSCMDNKD  GSCSVEYIPY  EAGTYSLNVT 1410        1420        1430        1440
YGGHQVPGSP  FKVPVHDVTD  ASKVKCSGPG  LSPGMVRANL 1450        1460        1470        1480
PQSFQVDTSK  AGVAPLQVKV  QGPKGLVEPV  DVVDNADGTQ 1490        1500        1510        1520
TVNYVPSREG  PYSISVLYGD  EEVPRSPFKV  KVLPTHDASK 1530        1540        1550        1560
VKASGPGLNT  TGVPASLPVE  FTIDAKDAGE  GLLAVQITDP 1570        1580        1590        1600
EGKPKKTHIQ  DNHDGTYTVA  YVPDVTGRYT  ILIKYGGDEI 1610        1620        1630        1640
PFSPYRVRAV  PTGDASKCTV  TVSIGGHGLG  AGIGPTIQIG 1650        1660        1670        1680
EETVITVDTK  AAGKGKVTCT  VCTPDGSEVD  VDVVENEDGT 1690        1700        1710        1720
FDIFYTAPQP  GKYVICVRFG  GEHVPNSPFQ  VTALAGDQPS 1730        1740        1750        1760
VQPPLRSQQL  APQYTYAQGG  QQTWAPERPL  VGVNGLDVTS 1770        1780        1790        1800
LRPFDLVIPF  TIKKGEITGE  VRMPSGKVAQ  PTITDNKDGT 1810        1820        1830        1840
VTVRYAPSEA  GLHEMDIRYD  NMHIPGSPLQ  FYVDYVNCGH 1850        1860        1870        1880
VTAYGPGLTH  GVVNKPATFT  VNTKDAGEGG  LSLAIEGPSK 1890        1900        1910        1920
AEISCTDNQD  GTCSVSYLPV  LPGDYSILVK  YNEQHVPGSP 1930        1940        1950        1960
FTARVTGDDS  MRMSHLKVGS  AADIPINISE  TDLSLLTATV 1970        1980        1990        2000
VPPSGREEPC  LLKRLRNGHV  GISFVPKETG  EHLVHVKKNG 2010        2020        2030        2040
QHVASSPIPV  VISQSEIGDA  SRVRVSGQGL  HEGHTFEPAE 2050        2060        2070        2080
FIIDTRDAGY  GGLSLSIEGP  SKVDINTEDL  EDGTCRVTYC 2090        2100        2110        2120
PTEPGNYIIN  IKFADQHVPG  SPFSVKVTGE  GRVKESITRR 2130        2140        2150        2160
RRAPSVANVG  SHCDLSLKIP  EISIQDMTAQ  VTSPSGKTHE 2170        2180        2190        2200
AEIVEGENHT  YCIRFVPAEM  GTHTVSVKYK  GQHVPGSPFQ 2210        2220        2230        2240
FTVGPLGEGG  AHKVRAGGPG  LERAEAGVPA  EFSIWTREAG 2250        2260        2270        2280
AGGLAIAVEG  PSKAEISFED  RKDGSCGVAY  VVQEPGDYEV 2290        2300        2310        2320
SVKFNEEHIP  DSPFVVPVAS  PSGDARRLTV  SSLQESGLKV
```

```
            2330          2340          2350          2360
       NQPASFAVSL    NGAKGAIDAK    VHSPSGALEE    CYVTEIDQDK 2370          2380          2390          2400
       YAVRFIPREN    GVYLIDVKFN    GTHIPGSPFK    IRVGEPGHGG 2410          2420          2430          2440
       DPGLVSAYGA    GLEGGVTGNP    AEFVVNTSNA    GAGALSVTID 2450    2460          2470          2480
       GPSKVKMDCQ    ECPEGYRVTY    TPMAPGSYLI    SIKYGGPYHI 2490    2500    2510          2520
       GGSPFKAKVT    GPRLVSNHSL    HETSSVFVDS    LTKATCAPQH 2530          2540          2550    2560
       GAPGPGPADA    SKVVAKGLGL    SKAYVGQKSS    FTVDCSKAGN 2570          2580          2590          2600
       NMLLVGVHGP    RTPCEEILVK    HVGSRLYSVS    YLLKDKGEYT

2610
       LVVKWGDEHI    PGSPYRVVVP
```

As used herein, the terms "filamin A modulator" or "FLNA modulator" refer to agents that impact the action of FLNA, by way of non-limiting example by stabilizing one conformation of FLNA at the expense of another, altering the structure of FLNA, altering the expression of FLNA polynucleotide or polypeptide. In various embodiments, the FLNA modulator is an inhibitory nucleic acid. In various embodiments, the FLNA modulator is a small hairpin RNA (shRNA). In various embodiments, the FLNA modulator is a small molecule that binds and reverses an altered conformation of filamin A. In various embodiments, the FLNA modulator is PTI-125.

As used herein, the term "epilepsy" refers to a condition in which a person has recurrent seizures. A seizure is defined as an abnormal, disorderly discharging of the brain's nerve cells (i.e. neurons), resulting in a temporary disturbance of motor, sensory, or mental function.

As used herein, the term "focal cortical dysplasia type II" or "FCD type II" means a disorder of brain development that leads to focal (or discrete) malformations of the cortex with specific cytoarchitecural alterations including (but not limited to) mislamination and neuron dysmorphogenesis. FCD type II can also refer to the malformation itself.

As used herein, "kartogenin" refers to a compound having formula 1:

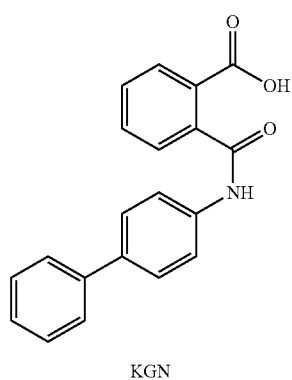 [SMILES: O=C(O)c1ccccc1C(=O)Nc1ccc(-c2ccccc2)cc1]

KGN or a salt, solvate or polymorph thereof.

As used herein, the term "tuberous sclerosis complex" or "TSC" means a genetic disorder resulting from mutations in the gene TSC1 or TSC2 and leads to a sprectrum of peripheral and neurological alterations, including, focal malformations of the cortex that are called cortical tubers.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention.

Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein "PTI-125" refers to the compound tested in ClinicalTrials.gov Identifier: NCT03748706, hereby incorporated by reference, or salts or solvates thereof. Further details regarding PTI-125 are available in Wang et al., PTI-125 binds and reverses an altered conformation of filamin A to reduce Alzheimer's disease pathogenesis, Neurobiology of Aging, Volume 55, July 2017, Pages 99-114.

As used herein, "treating a disease or disorder" means reducing the frequency or the severity with which a symptom of the disease or disorder is experienced by a patient. Disease and disorder are used interchangeably herein.

As used herein, the term "treatment" or "treating" encompasses prophylaxis and/or therapy. Accordingly the compositions and methods of the present invention are not limited to therapeutic applications and can be used in prophylactic ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Methods of Treating Disease

Without wishing to be limited by theory, the invention is based in part on the discovery that inhibition or modulation of FLNA treats epilepsy associated with hyperactivity of with hyerpactivity of the AKT-mTOR signaling pathway and MAPK pathway and the resultant formation of focal cortical malformations (called FCM above) by reducing or preventing seizures associated with these disorders. Accordingly, in one aspect the invention provides a method of treating seizures and thus epilepsy in a subject in need thereof, the method comprising providing to the subject an effective amount of a FLNA modulator. As shown in the examples and figures herein, shRNA mediated knockdown of FLNA and FLNA modulation by PTI-125 have been shown to reduce seizures in animal models.

The use of any FLNA modulator known in the art can be used effectively in various embodiments of the invention. Various FLNA modulators are described in U.S. Pat. Nos. 9,354,223, 8,580,809, 8,614,324 and 9,340,558 as well as U.S. publication No. 2014/028755 and PCT Publication No. WO 2014/028755. Accordingly, in various embodiments, the FLNA modulator is an inhibitory nucleic acid. In various embodiments, the FLNA modulator is PTI-125. In various other embodiments, the FLNA modulator is kartogenin.

In various embodiments the epilepsy is intractable epilepsy. As this term is used herein, intractable epilepsy refers to epilepsy which does not respond or does not satisfactorily respond to other drugs or methods of treatment or whose treatments are not appropriate. In various embodiments, the epilepsy is associated with focal cortical dysplasia (FCD) type II or tuberous sclerosis complex (TSC). FCD type 2 and TSC are conditions known to generate mTORC1 and MAPK (also called ERK1/2) hyperactivity during neurodevelopment and therefore result in the type of focal cortical malformations that FLNA inhibition is shown herein to treat. Accordingly, in various embodiments, the subject has FCD type 2 or TSC. A skilled person will recognize that the invention further provides methods of treating FCD type 2 or TSC by providing a subject in need thereof an effective amount of an FLNA modulator. In various embodiments, the FCDII is due to mutation upstream of mTORC1 but not mTORC1 itself. For example, rheb or TSC mutations lead to increases in both mTORC1 and MAPK activity and MAPK is responsible for FLNA increases In various embodiments the FLNA modulator is formulated in a pharmaceutical composition comprising at least one pharmaceutically acceptable excipient. The FLNA modulator can be administered by any method of administration known in the art. In various embodiments, the subject is a mammal. In various embodiments, the subject is a human. In various embodiments, the subject is a neonate, juvenile or adult.

In various embodiments, the effective amount of the FLNA modulator is about 0.001-5000 mg/kg, about 0.01-4000 mg/kg, about 0.1-3000 mg/kg, about 0.1-2000 mg/kg, or about 1-1000 mg/kg. In various embodiments, the effective amounts recited immediately above are effective amounts of PTI-125. In various embodiments, the effective amount of PTI-125 is about 0.1-5 mg/kg, about 0.3-3 mg/kg or about 0.5-2 mg/kg. These amounts refer to PTI-125 free base but a person of skill in the art will be readily able to adjust the dose for use with pharmaceutically acceptable salts or solvates of PTI-125. As illustrated in in detail below, in various embodiments the effective amount of the FLNA modulator is about 1-20 mg/kg. In various embodiments the effective amount is about 6-12 mg/kg of PTI-125 salt or about 4-8 mg/kg of PTI free base or equivalent.

In another aspect, the invention provides a method of treating focal cortical dysplasia (FCD) type II or tuberous sclerosis complex (TSC) in a subject in need thereof, the method comprising providing to the subject an effective amount of PTI-125.

In another aspect, the invention provides a method of treating focal cortical dysplasia (FCD), or tuberous sclerosis complex (TSC), or hemimegalencephaly in a subject in need thereof, the method comprising providing to the subject an effective amount of kartogenin.

Methods of Treating and Detecting Neurodegenerative Disease

FLNA modulators are recognized as inhibiting hyperphosphorylation of tau protein and therefore may be useful for the treatment of neurodegenerative diseases including but not limited to Alzheimer's disease and Parkinson's disease. Accordingly, in another aspect, the invention provides a method of inhibiting hyperphosphorylation of the tau protein that comprises the steps of administering to cells of the central nervous system in recognized need a FLNA-binding effective amount of kartogenin or a pharmaceutically acceptable salt.

FLNA modulators have been shown to alter the conformation of FLNA and shift the equilibrium of certain protein-protein complexes that are involved in Alzheimer's disease pathology in a manner that can be employed to detect Alzheimer's disease if present in a subject. Accordingly, in another aspect the invention provides a method for determining the likelihood of a living patient having Alzheimer's disease pathology (AD pathology) comprising the steps of determining the amount of one or more of a protein-protein complex i) α7nAChR/FLNA, ii) TLR4/FLNA and iii) α7nAChR/Aβ present in a first portion of a lymphocyte preparation from said living patient; determining the amount of said one or more of i) α7nAChR/FLNA, ii) TLR4/FLNA and iii) α7nAChR/Aβ present as a protein-protein complex in a second portion of said lymphocyte preparation, said second portion of said lymphocyte portion further containing admixed therein a FLNA binding-effective amount of kartogenin or a pharmaceutically acceptable salt thereof; comparing the values so determined, whereby a determined amount of said one or more of i) α7nAChR/FLNA, ii) TLR4/FLNA and iii) α7nAChR/Aβ present as a protein-protein complex in a second portion of said lymphocyte preparation that is significantly decreased in the presence of kartogenin or pharmaceutically acceptable salt thereof indicates that the patient had AD pathology at the time the body sample was taken, whereas no significant difference between the two determined values indicates that the patient was free of AD pathology at the time the body sample was taken.

Administration/Dosage/Formulations

The regimen of administration may affect what constitutes an effective amount. The therapeutic formulations may be administered to the subject either prior to or after the onset of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a patient.

The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of disease in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The present invention also includes a multi-layer tablet comprising a layer providing for the delayed release of one or more compounds of the invention, and a further layer providing for the immediate release of a medication for treatment of certain diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of the disease in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the modulator of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Study Design

The objectives herein were to investigate whether the expression of FLNA was increased in tissue from FCDII individuals and the cortices of mice modeling FCDII, and to then examine whether decreasing the amount of FLNA or its function was sufficient to reduce seizures. To decrease FLNA expression, an shRNA strategy was used as previously reported. The shRNA plasmid and FLNA antibody were validated. The quantity of shRNA to used was based on the previous study. To block FLNA function, a small molecule PTI-125 was used. The dosage of PTI-125 was determined by first testing the effects of PTI-125 on cell placement and morphology. The treatment paradigm was chosen to match several developmental milestones. Experimental and control animals were littermate although several litters had to be used for most experiment, and none were excluded from analysis at the time of harvest. Experimental animals were lost prior to or during seizure recordings either due to sudden death by seizure or due to technical issues with the recording system. No attempt was made to segregate results based on gender or sex. Analysis was performed blindly and seizure analysis was performed by two investigators. In addition, mice were randomly split into different groups for drug injection. Blinding was performed at multiple points during the experiments. For example, after video-EEG recording, the recording files were renamed for analysis by investigators blinded to the treatment condition.

Normality was checked with D'Agostino And Pearson normality test. Sample sizes were estimated based on our previous experience both for studying the anatomy and seizure activity. The sample size calculation was performed using power analysis with G*Power 3. For each set of experiment, the sample size was estimated for an effect size of 50% using SD calculated from the control population and a power at 80% ($\beta=0.2$) and an $\alpha$ of 0.05. Post-experiment, for FIG. 5G for example (effect of PTI-125 treatment from P29 to P54 on seizure frequency), using a Mann-Whitney test (2 groups, non-equal SD and not normal distribution, two tails), 13 mice in each group would be sufficient to reach significance with a power of 0.9 and an $\alpha$ of 0.05 for the presented data. Each experiment was reproduced at least three times with n greater or equal to three as detailed in Table 3. One mouse was removed for the video-EEG data in FIG. 3G. The mouse displayed no seizure despite bilateral electroporation of Rheb$^{CA}$ and after examination of the brain sections, very few electroporated cells were found per section (<10 cells). Electroporation was thus unsuccessful. The brain of every recorded mouse was examined post-EEG recording to make sure that the mouse with no seizure had proper electroporation.

Animals

All experiments were performed on CD-1 mice (Charles River) of either sex.

Human Tissue Sample

Human tissue was obtained directly from the surgery room and rapidly frozen in liquid nitrogen and then stored at $-80°$ C. (for immunoblotting and immunostaining) or fixed in 10% formalin (for immunohistochemistry). Patient information is provided in Tables land 2. The mean age of the control patients and patients with FCDII were 13.5±2.02 (n=11) and 15.08±2.47 years (n=12), respectively.

In Utero Electroporation and Plasmids

Each DNA plasmid was diluted in sterile PBS (pH 7.4). Timed pregnant mice (embryonic day, E15) were anesthetized with isoflurane. After exposing the uterine horns, ~1.5 µl of DNA solution, containing 0.1% fast green added as an injection tracer, was injected into the lateral ventricle via a pulled glass capillary. PBS-soaked tweezer-type electrodes (model 520, BTX) were then positioned on the head of the fetuses across the uterine wall and 6 square-pulses at 42 mV and 50 ms duration every 950 ms were applied using a pulse generator (ECM830, BTX). At birth, mice were prescreened for successful electroporation by detecting the expression of fluorescent protein markers on a fluorescence-enabled stereo microscope (SZX16, Olympus). Morphology and seizure data in different conditions (Flna vs Luciferase shRNA or vehicle vs PTI-125 treatment) were compared between littermate mice. For most experiments, mice received unilateral electroporation, except for experiments in FIG. 4F (P8-P65 PTI-125 treatment on seizures) for which mice received bilateral electroporation.

Transcardial Perfusion and Immunofluorescence

Mice: Mice were transcardially perfused with PBS followed by 4% paraformaldehyde. Brains were then dissected and post-fixed in 4% paraformaldehyde for 24 hours before being transferred to a solution of 3% agarose solution in PBS. These were then sectioned coronally on a vibratome at a thickness of 50 µm. For immunofluorescence, free-floating sections were incubated for 1 hour in a blocking solution (2% bovine serum albumin and 0.1% Triton-X in PBS) at room temperature and then incubated with primary antibodies (Table 5) overnight at 4° C. Sections were washed with PBS+0.05% Tween 20 and then placed in blocking solution containing secondary antibodies for 1 hour at room temperature. All images were taken using an FV1000 confocal microscope (Olympus).

Humans: For Immunohistochemistry analysis, human samples were frozen in liquid nitrogen or fixed in 10% formalin and embedded in paraffin for preparing serial sections (4 µm-thick) that were then deparaffinized and rehydrated by immersion in xylene followed by ethanol gradients. Slices were soaked in citrate solution followed by boiling in a microwave (for antigen unmasking) and washed in 3% hydrogen peroxide. Tissue sections were incubated with primary antibodies (Table 5) overnight at 4° C. in a moist chamber. After washing with PBS, slices were incubated with secondary antibody for 30 mins at room temperature. Sections were mounted after dehydration.

Quantification of Neuronal Distribution, Soma Size, Staining Intensity

Quantification of the number of layer 2/3 neurons in the anterior cingulate cortex, the boundary between layer 2/3 and layer 5 was determined using ER81 staining, which labels layer 5 (FIGS. 14A-14B)Soma size was quantified by outlining the soma of GFP+ cells and measuring the area using ImageJ. Intensity of phospho-S6 and FLNA in sections was quantified by outlining somas of cells and measuring the mean gray value. Then, the values in electroporated cells (in mice) or SMI-311-positive cells (in humans) were normalized to those in non-electroporated cells or unstained cells surrounding electroporated cells to control for variability of staining between sections.

Sparse Neuron Electroporation and Quantification of Dendritic Trees

To analyze neuronal morphology and, in particular dendritic trees, only a few neurons per section were labeled using a Cre-based strategy as previously reported. More specifically, an inducible DsRed2 vector (pCAG-LoxP-stop-LoxP-DsRed2, pCALNL-DsRed2) combined with a Cre vector (pCAG-Cre) was used at very low concentration (1 ng/µl). The Cre plasmid led to DsRed expression in only 3-5 neurons per slice allowing to cleanly analyze the dendritic morphology of individual neurons (FIGS. 15A-15C)Images of DsRed-expressing basal dendrites were acquired in coronal sections using a Fluoview 1000 confocal microscope with a 20× objective. Basal dendrites were traced with simple neurite tracer software (FIJI and Neuronstudio). Sholl analyses were carried out using the number of intersections in 10-µm-increment concentric circles as a measure of morphological complexity. Z stacks from three different square fields of view were taken from three different sections. Analysis was performed blindly with more than four animals and more than 20 cells per condition (see Table 3 for actual n number).

Neuro2a Cell Culture and Transfection

Neuro2a cells were grown at 37° C. with 5% $CO_2$ in a complete media consisting of high glucose DMEM (Gibco, #11965-092), 5% heat-inactivated fetal bovine serum (Gibco, #16140071), and 1% penicillin-streptomycin. Cells were plated in 12 well culture plates (Corning, #0720082) and transfected when they reached ~70% confluence. Transfection was done using PolyJet transfection reagent (Signagen, SL100688) according to the manufacturer's instructions. Cells were lysed 72 hours after transfection for all experiments.

Nucleofection and Culture of E15 Cortical Neurons

The medial prefrontal cortexes of E15 pups were dissected out and incubated in papain digestion solution (Worthington, #LK003176) for 15 min at 37° C. The cortexes were then transferred to plating medium (MEM supplemented with 5% FBS, 0.45% glucose) and dissociated by using glass pipette. Following dissociation, cells were nucleofected using a Mouse Neuron Nucleofector kit (Lonza, #VPG-1001) according to the manufacturer's instructions. Cells were finally plated on poly-D-lysine-coated 6-well plates (BD Biosciences, #354413). The medium was changed to neuronal maintenance medium (neurobasal with 1×B27 and 1×GlutaMAX-1) 2 h after plating. Protein extraction and western blots were performed 14 days after nucleofection.

Western Blot

Human and mouse samples were lysed in RIPA buffer (Thermo fisher, #89900) with protease/phosphatase inhibitor cocktail (Cell Signaling Technology, #5872), 5 mM EDTA, and 20 units/ml DNase I (Roche). All lysates were run on Tris-glycine gels (Bio-Rad, #456-1086 for mouse samples and #456-1046 for human samples). Proteins were transferred to PVDF and blocked in 5% milk and incubated with primary antibodies (concentrations of primary antibody are listed in Table 5). HRP-conjugated anti-rabbit or anti-mouse were used as secondary antibodies. Phosphorylated and total proteins were blotted on the same membrane after stripping (Thermo fisher, #21059). All density measurements were performed using NIH Image J software. In the case where cross-blot normalization was required a reference sample was loaded on each gel to account for inter-gel variability (FIGS. 11A-11B).

EEG Headmount Implantation

Prefabricated EEG headmounts (Pinnacle Technology, cat. no. 8201-EEG) were implanted in 6 to 8 weeks old mice. Mice were anesthetized with isoflurane and positioned on a stereotaxic frame using ear bars. A rostro-caudal midline incision was made in the skin to expose the skull surface. Four pilot holes (two bilateral holes 1 mm anterior to bregma and two bilateral holes 5 mm posterior to bregma, each 1.5 mm lateral to sagittal suture), was tapped through the skull to dura using a microdrill (Roboz Surgical Instrument, #RS6300). The headmount was attached on top of the skull by threading four stainless steel screws (Pinnacle Technology, cat. no. 8209) into the pilot holes. Silver conductive paint (Electron Microscopy Science) was applied around the screw threads to ensure a solid connection with the headmount. The entire implant was insulated using dental acrylic. Mice were allowed to recover in their home cage for seven days before video-EEG monitoring.

Video-EEG Recordings and Analysis

Mice were housed in individual recording chambers in a light-, temperature- and humidity-controlled room during video-EEG monitoring. Mice were freely moving inside the chambers and had ad libitum access to food and water. Synchronous video-EEG recording was acquired using a three-channel EEG tethered system (Pinnacle Technology, cat. no. 8200-K1-iSE3) and Sirenia Acquisition software (Pinnacle Technology). Mice were continuously recorded 24 hours/day for 5-6 consecutive days or 31-45 days.

Seizure frequency and duration were analyzed using Sirenia Seizure Basic software (Pinnacle Technology). All analyses were performed blinded to experimental groups by at least two investigators. The entire EEG traces were manually reviewed for the occurrence of seizures, defined as a sudden onset of high amplitude activity with a characteristic pattern of progressive frequency and amplitude changes over the course of the event lasting≥10 sec. Seizure onset was defined by high amplitude firing>2× baseline and seizure termination was defined by a return to baseline activity. Video data were inspected for behavioral correlates including myoclonic jerks, tonic-clonic activities, convulsions, and loss of postural control (rearing and falling) and were used as secondary verification of seizures. For each individual animal, mean number of seizures per day was obtained by dividing the total number of seizures by the total number of recording hours and multiplied by 24.

Drug Injections

PTI-125 was dissolved in saline at a concentration of 2.4 mg/ml. Mice received two intraperitoneal injections of 6 or 12 mg/kg PTI-125 every day. Saline was used as vehicle treatment.

Statistical Analyses

All analyses were conducted blindly knowing only the arbitrarily assigned animal ID (independent of electroporation condition). Statistical tests and plots were performed using Prism 7 (GraphPad Software, Inc.). Statistical significance was determined using Student's t-test (two-tailed, paired or unpaired), one-way ANOVA, two-way ANOVA (repeated measures, with Sidak or Tukey multiple comparisons post-test), Wilcoxon matched-pairs signed rank test, Mann Whitney U test (two-tailed), and Fisher Exact test, with $P<0.05$ for significance for all experiments. Data are presented as mean±SEM. Table 3 details the statistical test used for each data set as well as the n.

Example 1: FLNA is Increased in Patients with FCDII and in $Rheb^{CA}$ Mice Modeling TSC and FCDII Cortical tissue samples from 17 patients with FCDII who underwent surgery for epilepsy were obtained (Table 1). Every patient had FCM detected on MRI scans (two examples are shown in FIG. 1A) and underwent electroencephalogram (EEG) recording with a combination of subdural grid and depth electrodes prior to FCM resection. All patients were identified as FCDII post-surgery based on pathological examination of the hematoxylin-stained resected tissue and identification of hallmarks of FCDII, including cortical dyslamination and the presence of cytomegalic, dysmorphic neurons (Table 1). The distinction between FCDIIa and FCDIIb was based on the absence or presence of balloons cells, respectively. For the FCDII tissue examined by immunohistochemistry (n5), the presence of dysmorphic cells was confirmed, including classical multinucleated balloon cells, and an increase in phosphorylated ribosomal protein S6 (phospho-S6), a read-out of mTORC1 activity (FIG. 1B, and FIGS. 9A-9F). These enlarged cells had increased expression of FLNA compared to surrounding normal-sized cells (FIG. 1C and FIGS. 9A-9F). To verify that cells expressing FLNA were neurons, FLNA and SMI-311 were co-immunostained for, a marker of cytomegalic, dysmorphic neurons. All SMI-311-positive neurons were immunoreactive for FLNA (FIGS. 1D-1F, and FIGS. 10A-10E) and displayed significantly increased FLNA intensity compared to surrounding cells (P<0.0001, FIG. 1G).

Figure 16A:
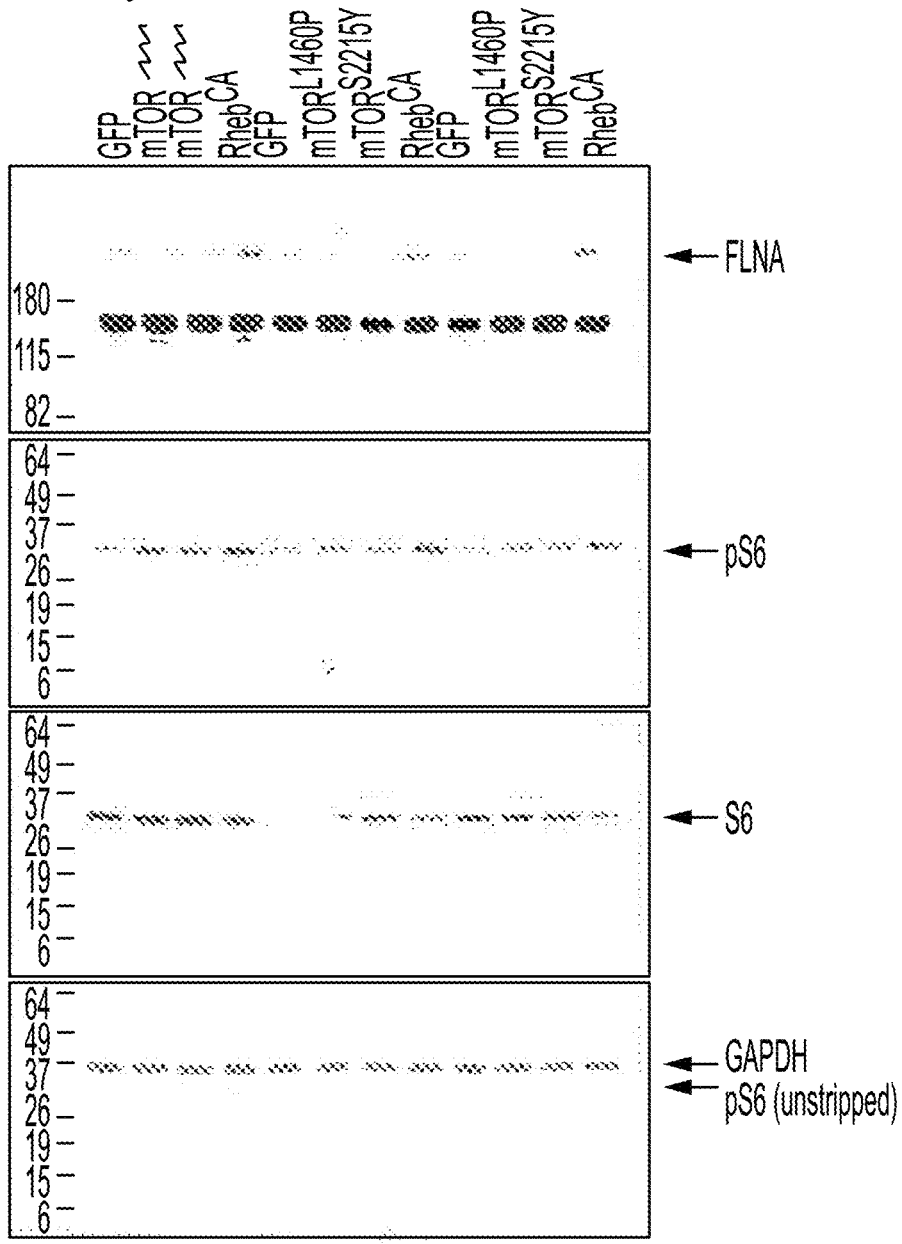
Figure 16B:
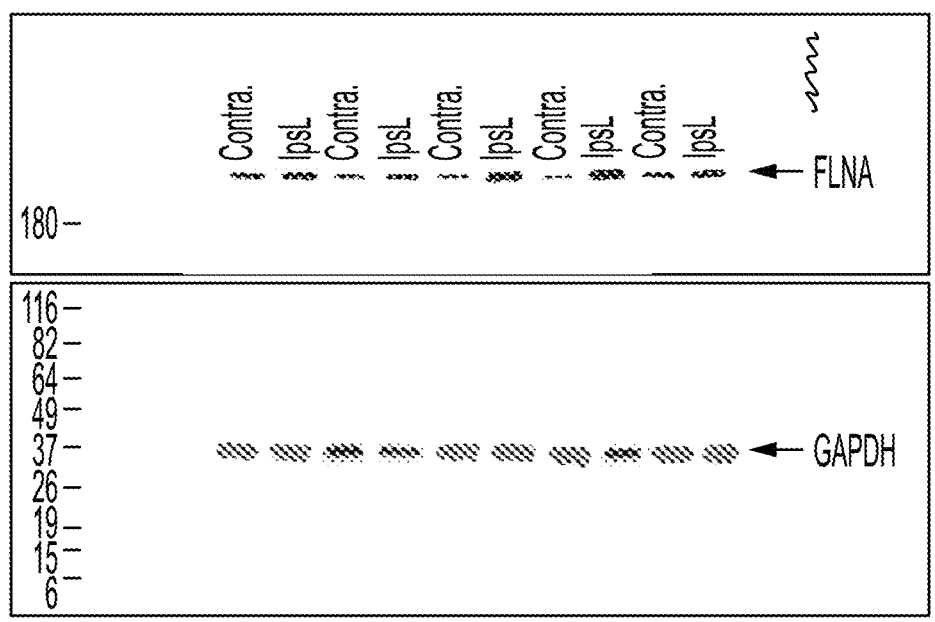
Figure 16C:
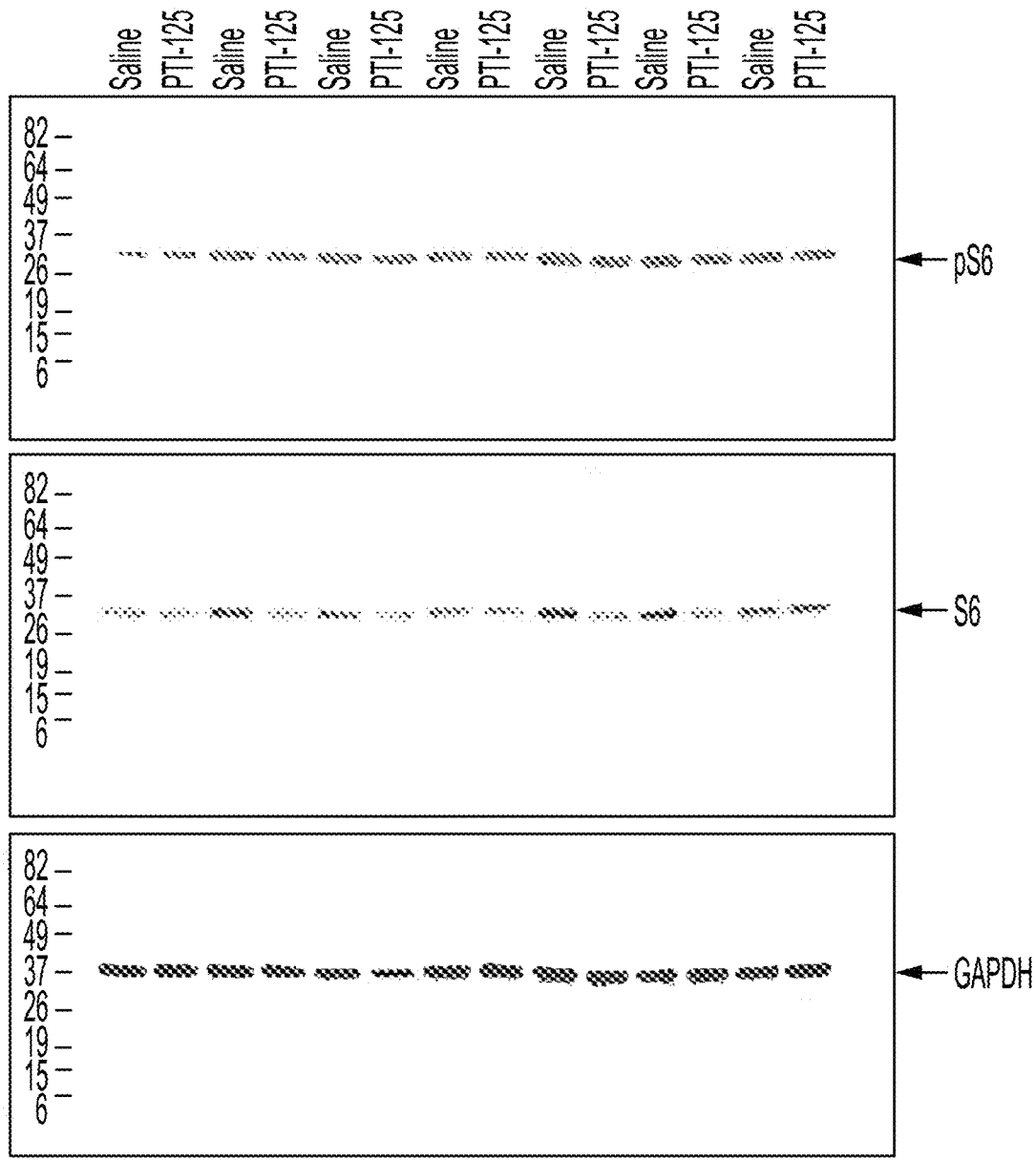
Figures 1, 16D:
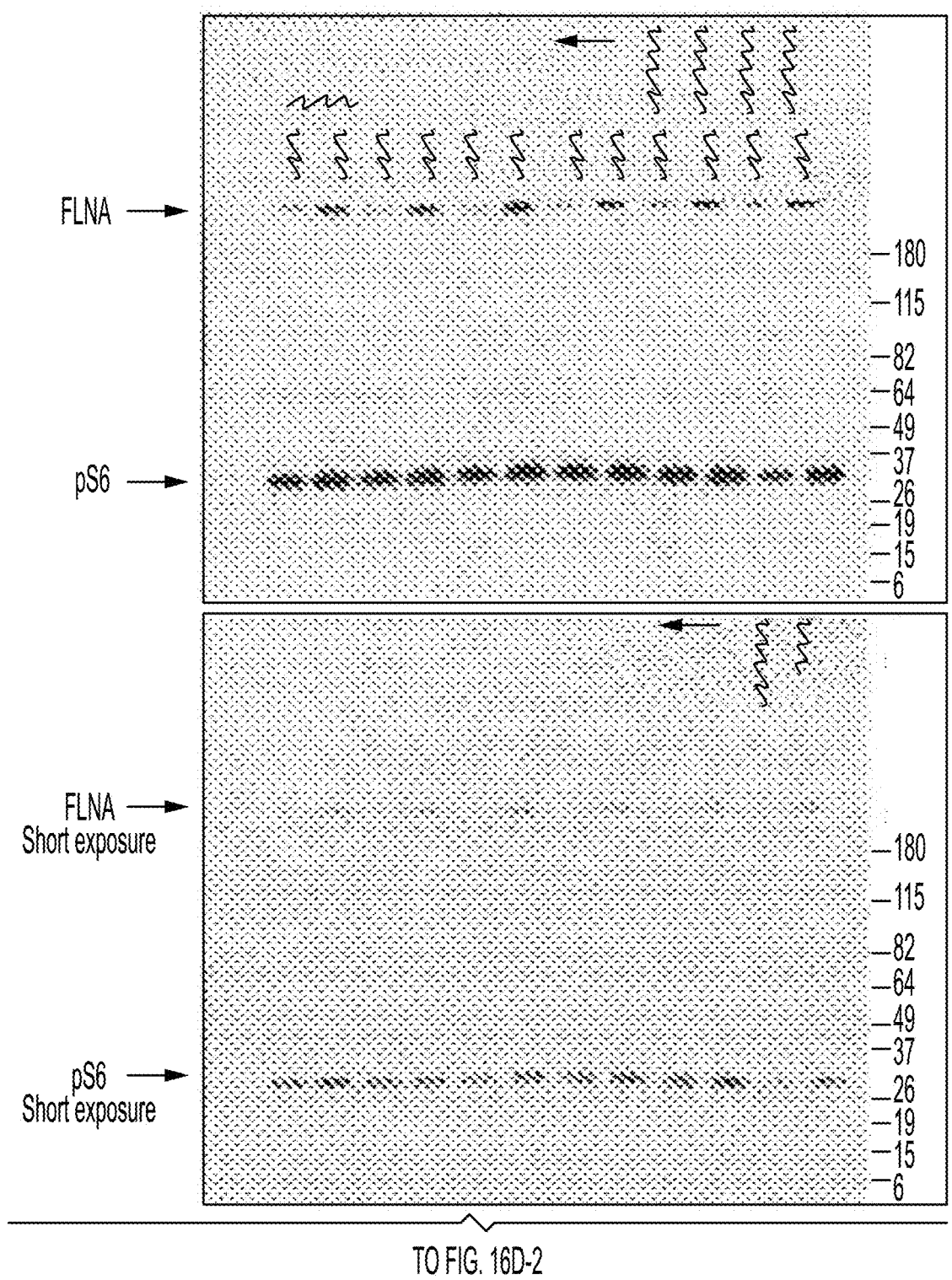
Figures 2, 16D:
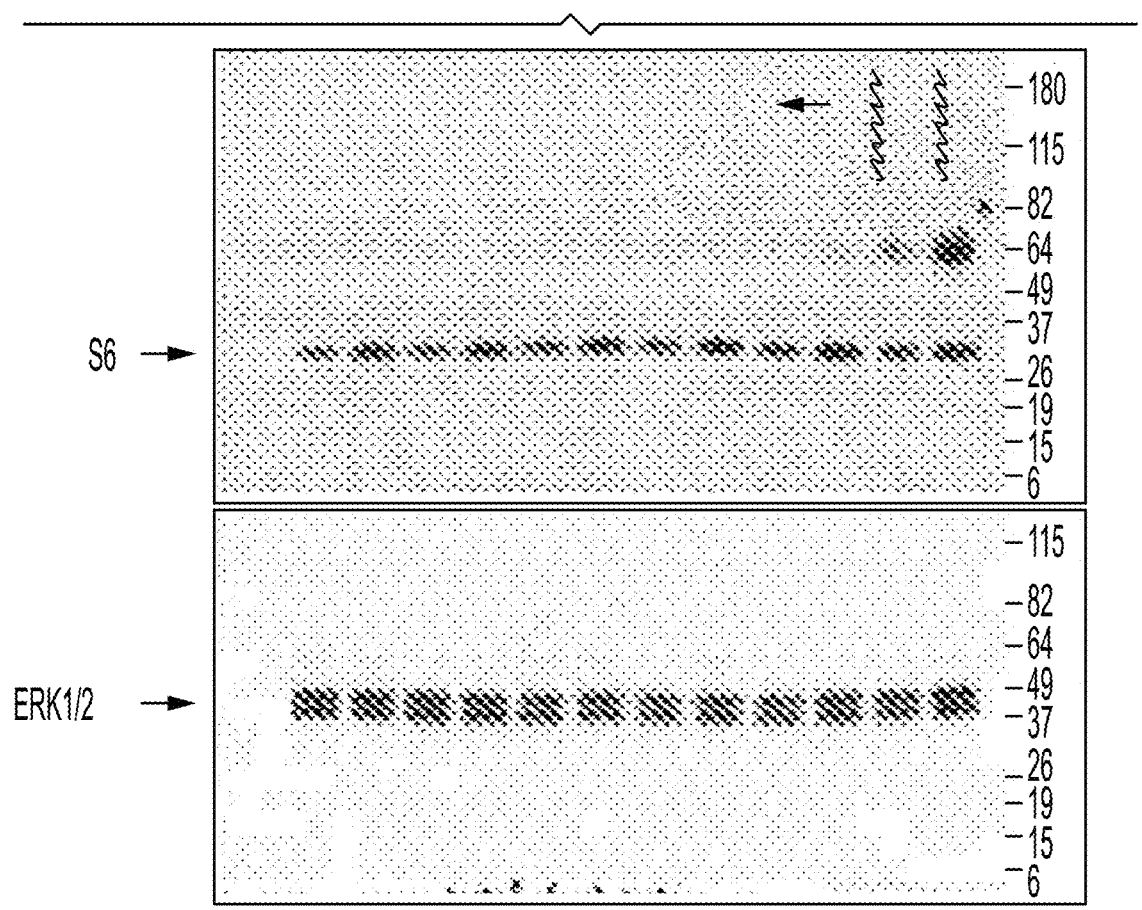

To quantify FLNA expression in patients with FCDII (n=12) compared to controls, tissue from age-matched control patients who underwent surgery for brain trauma (n=11, Table 2) were obtained and immunoblotting for FLNA was performed (FIG. 1H). As a group, FCDII tissue from 12 patients displayed significantly (P=0.009) increased amount of FLNA compared to control cortical tissue (FIG. 1I and FIGS. 11A-11B; numbers on top of the blot correspond to patient numbers in Table 1). In light of the variability of the western blot data (ranging from 0.57 to 2.31× control values), it was examined whether the amount of FLNA was correlated with the age of seizure onset, the duration of epilepsy history, and the diagnosis of FCDIIa versus FCDIIb. No correlation was found between the amount of FLNA and these parameters (FIGS. 12A-12C). Another parameter that may contribute to the variability in FLNA expression is the identity of the mutant genes. Indeed, as previously reported the increase in FLNA induced by Tsc1 loss or $Rheb^{CA}$ overexpression was mTORC1-independent, suggesting that mutations in mTORC1 itself do not contribute to increases in FLNA. This hypothesis was tested in cultured neurons (14 days in vitro) nucleofected with two plasmids encoding mTORC1 with gain-of-function mutations reported in patients with FCDII or $Rheb^{CA}$. The two mTORC1 mutations did not increase FLNA compared to control whereas $Rheb^{CA}$ did, despite that all three conditions significantly increased phospho-S6 (P<0.0003, FIGS. 2A-2C and FIGS. 16A-16D). Although the mutations in the human tissue used for immunoblotting were not identified, these data may explain some of the variability in the amount of FLNA in human samples. These data suggest that FLNA could be increased in patients with TSC or FCDII resulting from PI3K-Rheb pathway gene mutations but not from mTORC1 mutations.

Figure 2A:
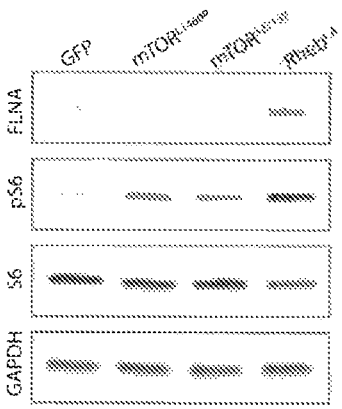
FIG. 2A-2H depict that FLNA expression is increased in mouse cortices containing $Rheb^{CA}$-induced FCM.
Figure 2B:
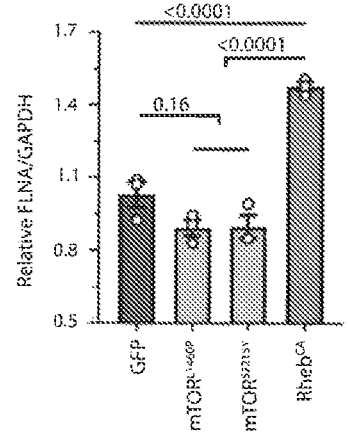
Figure 2C:
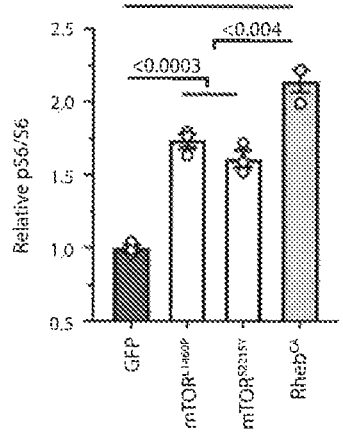
Figure 2D:
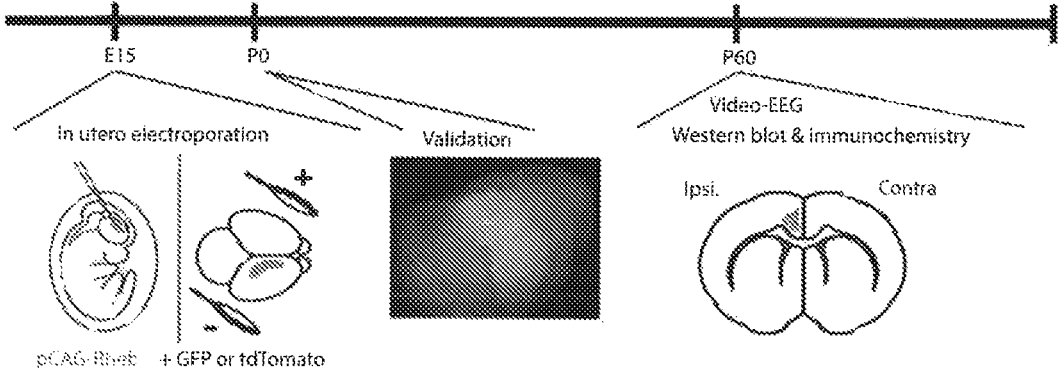
Figure 2E:
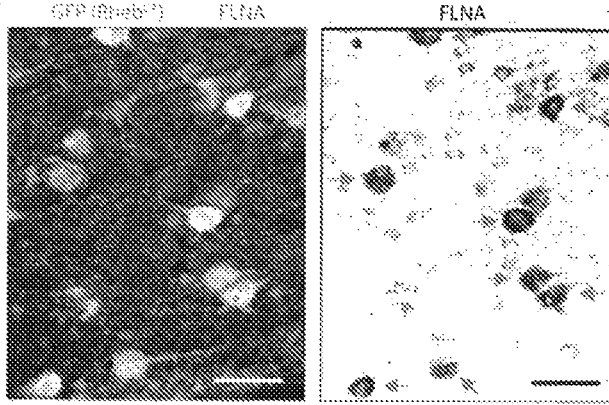
Figure 2F:
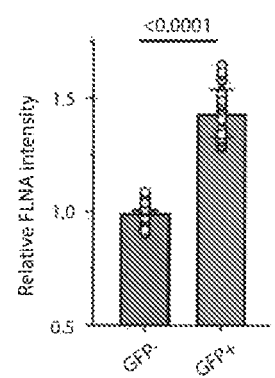
Figure 2G:
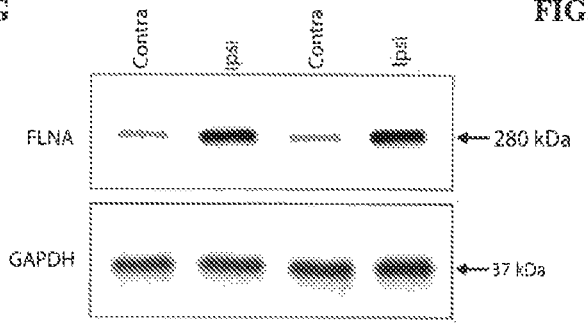
Figure 2H:
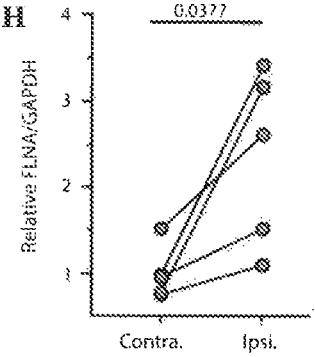

Prior to examining the contribution of increased FLNA to seizures, it was examined whether FLNA was increased in our $Rheb^{CA}$ mouse model of TSC and FCDII-like FCM associated with seizures. This model was generated using in utero electroporation (IUE) of plasmids encoding $Rheb^{CA}$ and the fluorescent reporter green fluorescent protein (GFP) in the medial prefrontal cortex at embryonic day (E) 15 (FIG. 2D). In control, littermate mice, tdTomato was expressed instead of $Rheb^{CA}$. The cortex of $Rheb^{CA}$-expressing mice displayed the cytoarchitectural hallmarks of human FCM, including cell misplacement, increased soma size, and neuronal dysmorphogenesis (FIGS. 3A-3D). The animals exhibited daily, convulsive seizures as monitored by video-EEG at 2-3 months of age. FLNA immunostaining in cortical sections of $Rheb^{CA}$-expressing mice illustrated increased FLNA in $Rheb^{CA}$-expressing cells (GFP+) compared to surrounding, non-electroporated (GFP−) cells (FIGS. 2E and 2F). In addition, immunoblots confirmed increased FLNA in the FCM-containing cortices (ipsilateral) compared to the contralateral (non-electroporated) cortices (FIGS. 2G and 2H, and FIGS. 16A-16D).

Example 2: Normalizing FLNA Expression in Dysmorphic Neurons of mTORC1-Driven FCM Attenuates Seizure Frequency It was examined whether normalizing FLNA expression would prevent some of the cytoarchitectural abnormalities found in the experimental FCM. To decrease FLNA expression in $Rheb^{CA}$-expressing neurons, a short hairpin RNA (shRNA) against Flna or Luciferase (control) were co-expressed using E15 IUE. A 1:1 ratio of FLNA shRNA to $Rheb^{CA}$ plasmid concentration was used because it was previously reported that this ratio fully normalized FLNA expression in $Rheb^{CA}$-containing cortical neurons in vitro. Cell placement and morphology were analyzed at postnatal day (P) 28 as previously reported. Flna shRNA partially, but significantly, prevented neuronal misplacement (from 50% to 23% of misplaced cells versus only 2% in control, P<0.0001, FIG. 3A), increased soma size (from 372% to 250% of control, P<0.0001, FIG. 3B), and dendritic dysmorphogenesis (from 194% to 130% of control total dendritic length, P<0.0001, FIGS. 3C and 3D. Considering that increased soma size is often used as a read-out of increased mTORC1 activity and that decreasing FLNA expression reduced soma size, it was examined whether Flna shRNA would affect the amount of phospho-S6, a more direct read-out of mTORC1 activity than soma size. Flna shRNA did not prevent increased phospho-S6 intensity in vivo (FIG. 3H). This was further confirmed in vitro in Neuro2a cells in which Flna shRNA did not reduce $Rheb^{CA}$-induced increased S6 phosphorylation (FIGS. 13A-13B). In addition, although Flna shRNA reduced $Rheb^{CA}$-induced increase in soma size, it did not normalize it (still increased by 250%) consistent with persistent hyperactive mTORC1 in the Flna shRNA condition. Finally, video-EEG recordings of $Rheb^{CA}$-expressing mice for 5 days starting at P61 followed by pathological analysis of the tissue (FIGS. 3E and 3F) was obtained. Mice expressing Flna shRNA in $Rheb^{CA}$-expressing neurons displayed a significantly lower seizure frequency (by 83%, P<0.0001) compared to mice expressing luciferase shRNA (mean of 2.2 vs 12.6 seizures/day, FIG. 3G). In addition, whereas 4 out of 16 mice died in the control group, no mice died in the Flna shRNA group (out of 10 mice). Both groups of mice (Flna and Luciferase shRNA) had similar increases in phospho-S6 expression (FIG. 3H). These data suggest that differences in seizure activity between the control and Flna shRNA condition were not due to variations in $Rheb^{CA}$-induced mTORC1 activation, and thus FCM features, and that the rescue of cytoarchitectural abnormalities by Flna shRNA was independent of mTORC1.

Figure 4A:
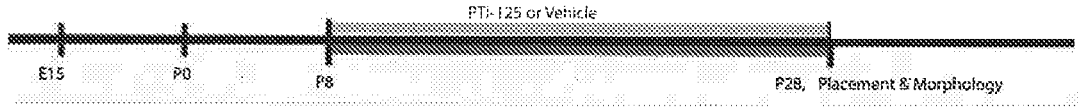
FIGS. 4A-4J depict that treatment with a small molecule modulator of FLNA, PTI-125, prior to seizure onset partially prevents cytoarchitectural abnormalities and reduces seizure activity.
Figure 4B:
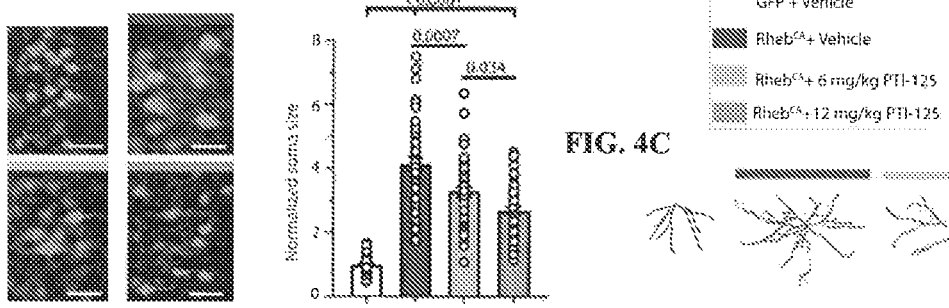
Figure 4C:
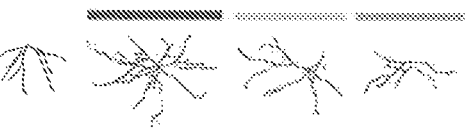
Figure 4D:
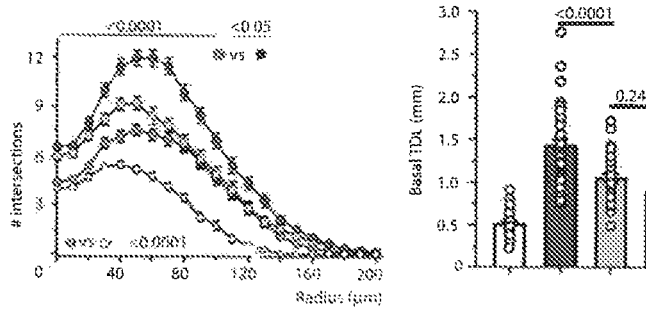
Figure 4E:
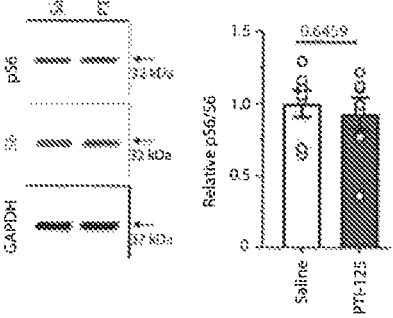
Figure 4F:
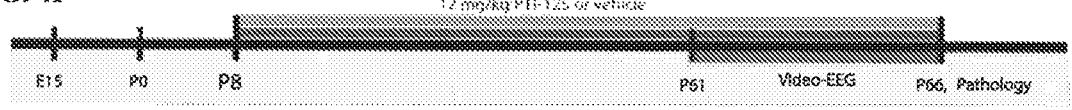

Example 3: Long-Term Treatment with a Small Molecule Modulator of FLNA, PTI-125, Prior to Seizure Onset Partially Prevents Neuronal Dysmorphogenesis and Reduces Seizure Activity The therapeutic potential of modulating aberrant FLNA activity via a small FLNA-binding molecule, PTI-125 was investigated. PTI-125 was derived from an iterative in silico/in vitro screening process against a known pentapeptide region of FLNA that was identified in an earlier study. PTI-125 has been reported to bind native FLNA as well as aberrant FLNA in Alzheimer's disease with picomolar and femtomolar affinity, respectively, and is currently in clinical trials for Alzheimer's disease (ClinicalTrials.gov no. NCT04079803). Twice-daily intraperitoneal injections of 6 or 12 mg/kgPTI-125 (salt form) were given to $Rheb^{CA}$-expressing mice from P8 to P28 to test efficacy at preventing the FCM-associated cytoarchitectural abnormalities (FIG. 4A). P8 was chosen because it corresponds to a newborn human and by P28 dendritic development is complete. PTI-125 at 6 and 12 mg/kg partially rescued neuronal soma size and dendritic dysmorphogenesis, with slightly greater efficacy at the 12 mg/kg dose (FIG. 4B-4D). It was also found that phospho-S6 expression in the cortex of nonelectroporated mice were not affected by PTI-125 (12 mg/kg) treatment (FIG. 4E and FIGS. 16A-16D). Next was examined the efficacy of long-term (P8-P65) PTIs-125 treatment at 12 mg/kg on seizure activity that was recorded at P61 to P66 using video-EEG (FIG. 4F). Littermate mice were randomly split into two groups, receiving PTI-125 or saline vehicle (intraperitoneal injections twice daily). PTI-125 treatment significantly reduced seizure frequency compared to vehicle treatment (5.1 vs 1.4 seizures/day, P=0.003, FIG. 4G). This treatment did not affect body weight (FIG. 4H). In addition, cell misplacement and phospho-S6 intensity in brain sections from recorded mice were not affected by PTI-125 treatment (FIGS. 4I and 4J). Hence, the reduced seizure activity in PTI-125-treated mice was not due to technical issues with IUE or differences in mTORC1 activation between the two groups of mice. Thus, PTI-125 treatment prior to seizure onset efficiently reduces seizure frequency by 73% independently of mTORC1.

Figure 5A:
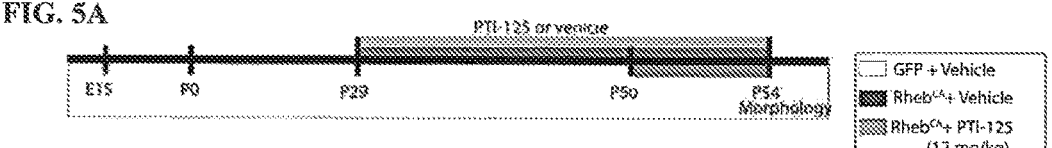
FIGS. 5A-5K depict that treatment with a small molecule modulator of FLNA, PTI-125, after seizure onset alleviates neuronal dysmorphogenesis and seizure activity.
Figure 5B:
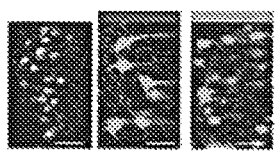
Figure 5C:
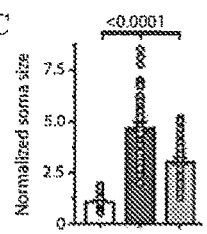
Figure 5D:
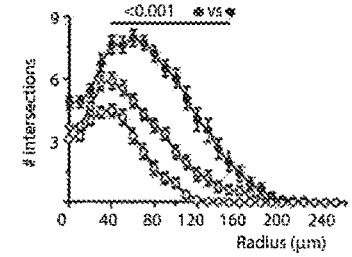
Figure 5E:
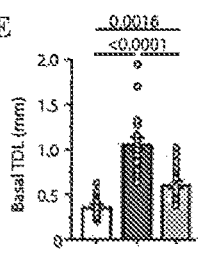
Figure 5F:
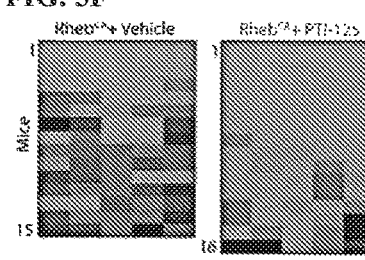

Example 4: PTI-125 after Seizure Onset Rescues Neuronal Dysmorphogenesis and Decreases Seizure Activity Next tested was whether a treatment with PTI-125 after the onset of seizures could rescue some of the morphological abnormalities and seizure activity. In our mouse model, Racine grade 4-5 seizures are visible by P21. A 26-day treatment with PTI-125 from P29 to P54 (3-week treatment, FIG. 5A) partially, but significantly, rescued increased soma size (P<0.0001, FIGS. 5B and 5C) and dendritic dysmorphogenesis (P<0.0001, FIG. 5D and FIG. 5E). To assess efficacy on seizure activity, video-EEG recordings were obtained at the end of the treatment (P5O-P54). PTI-125-treated mice displayed a significantly lower seizure frequency by 69% (P=0.0158) compared to vehicle-treated mice (0.84 vs 2.7 seizures/day, FIGS. 5F and 5G). Then assessed was the effect of PTI-125 on seizure activity in young adult (P61-P106) mice that were recorded during saline injections and subsequently switched to PTI-125 injections to assess treatment effects in the same mice (FIG. 5H). Recorded also were randomly selected littermate mice that were treated with vehicle from P61 to P92 and observed that seizure frequency increased over time (FIGS. 5I and 5J). In that same timeframe, corresponding to a 20-day PTI-125 treatment, littermate mice that were switched from vehicle to PTI-125 after 12 days of recordings did not have the increase in seizure frequency observed in the vehicle group (FIGS. 5I and 5J). Moreover, extended recording of the PTI-125-treated mice showed that a 33-day treatment led to a significant 60% reduction (P=0.0156) in seizure frequency (mean of 1.6 vs 3.9 seizures/day, FIG. 5K). Thus, PTI-125 treatment after the onset of seizures in either juvenile or adult mice decreased seizure frequency and prevented the worsening of seizure activity observed over time in vehicle-injected adult mice.

Figure 4G:
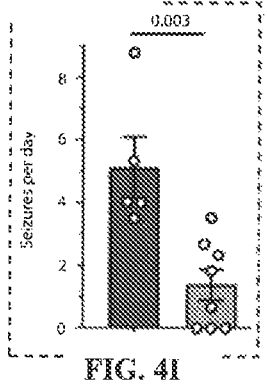
Figure 4H:
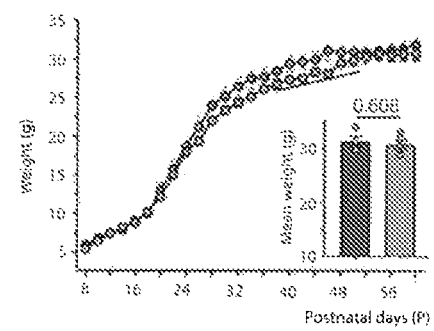
Figure 4I:
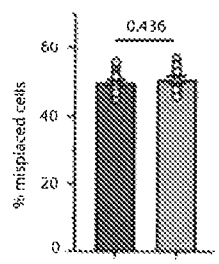
Figure 4J:
Figure 5G:
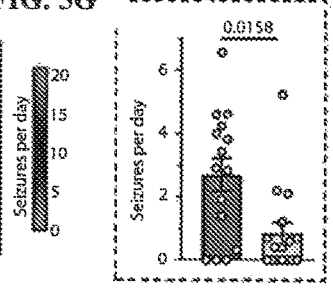
Figure 5H:
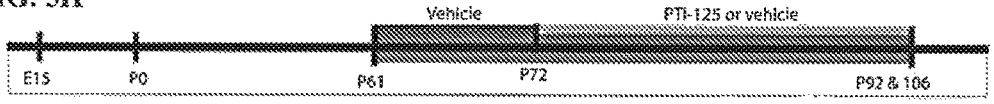
Figure 5I:
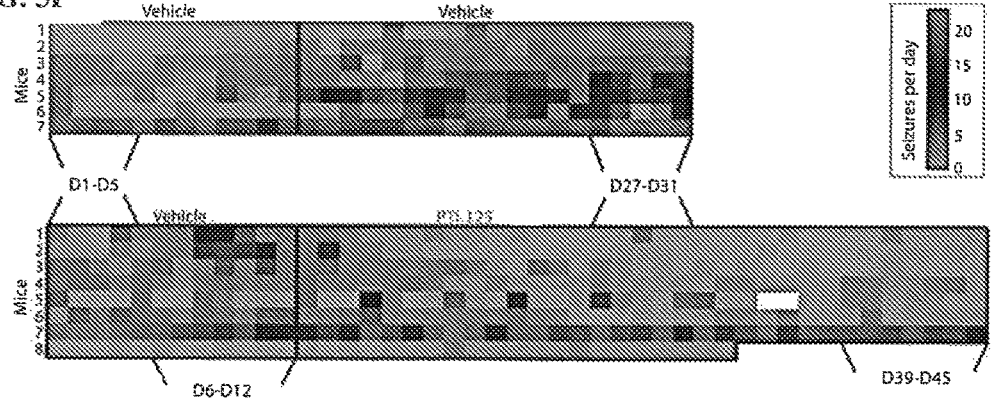
Figure 5J:
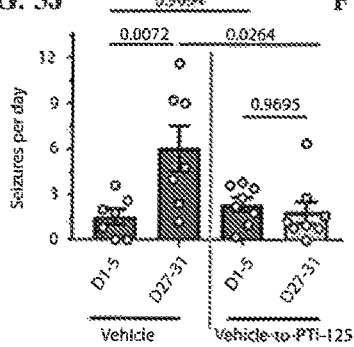
Figure 5K:
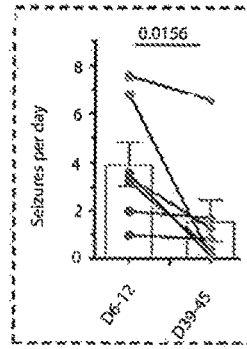

Finally, the seizure data obtained for all the PTI-125 treatments were combined and compared to their corresponding vehicle treatments (data from FIGS. 4G, 5G, and 5K corresponding to P8-P65, P29-P54, and P71-P91 treatments, respectively). PTI-125 treatments significantly increased the number of seizure-free mice (35% vs 11%, P=0.0343, FIG. 6A). In addition, mice treated with PTI-125 (n=32) exhibited an overall 66% reduction in seizure frequency compared to vehicle-treated littermates (n=27), illustrated in a heatmap (FIG. 6B) and scatter graph (P<0.0001, FIG. 6C).

Example 5

It was found that cortical tissue from patients with FCDII displayed increased FLNA. In addition, the increase in FLNA was observed in SMI-311-immunopositive enlarged neurons and cells resembling balloon cells. These findings are in agreement with study reporting increased FLNA expression in Tsc1$^{null}$ neurons in vivo and Rheb$^{CA}$-expressing cortical neurons in vitro as well as in cortical tissue from individuals with TSC. However, there was a marked variability in the amount of FLNA in human FCDII samples, including samples that expressed similar FLNA amount to that in controls. This variability could be explained by the fact that mutations leading to increased Rheb activity led to FLNA increases whereas gain-of-function mutations in mTORC1 did not. Although the genetic status of the patients was not known, it is possible that some patients had mTORC1 mutations that would not result in increased FLNA expression. The lack of effect of hyperactive mTORC1 on FLNA expression is consistent with our previous observations that increased FLNA expression was due to increased transcriptional activity downstream of hyperactive MEK/MAPK independently of mTORC1. In Rheb$^{CA}$ mice modeling the pathology seen in TSC and FCDII, FLNA expression was also increased in Rheb$^{CA}$ neurons and the cortex containing Rheb$^{CA}$ neurons.

Using an shRNA against Flna, it was found that decreasing FLNA expression in Rheb$^{CA}$ neurons alleviated their misplacement and dysmorphogenesis, including increased soma size and dendritic complexity. The rescue of soma size was unanticipated because knocking down FLNA did not decrease mTORC1 activity, which is well-known to regulate cell size. The mechanism of FLNA's role in cell size regulation is not known; FLNA could affect actin cross-linking and/or the activity of many binding partners, including previously unrecognized partners in the hyperactive mTORC1 condition. Identifying how knocking down FLNA alters soma size is outside the scope of the present study. Nevertheless, finding that normalizing FLNA expression did not rescue mTORC1 hyperactivity highlights that FLNA acts via a different mechanism than the mTORC1 blocker, rapamycin, to alleviate cellular abnormalities in TSC and FCDII conditions. Ultimately, normalizing FLNA expression using Flna shRNA in Rheb$^{CA}$-expressing mice led to a decrease in seizure activity (by 83%) compared to control. This finding seems to contradict the fact that mTORC1 activity is required for epilepsy since rapamycin blocks seizure activity and is also sufficient for epilepsy since patients with FCDII with gain-of-function mTORC1 mutations display seizures and expressing plasmids encoding hyperactive mutant mTORC1 in mice leads to seizures. One possible explanation for this discrepancy is that FLNA interferes with the translation machinery downstream of mTORC1, possibly through cytoskeletal reorganization (considering that poly(A) mRNA colocalized with FLNA or its interaction with disease-specific binding partners regulating cap-dependent translation. FLNA is indeed an actin-cross linking molecule, has multiple binding partners, and acts as a scaffolding platform inside cells where molecules can interact. Considering that increased soma size and dendritic tree require increased translation, a partial reduction of these defects by normalizing FLNA further suggests an interaction between FLNA and translation. This putative function of FLNA should be investigated in future studies. Finally, although the parallel rescue of some of the morphological abnormalities and seizure activity by Flna shRNA implies that these abnormalities contribute to epileptic seizures, it is possible that these rescues are coincidental and rescuing other intracellular processes by Flna shRNA may prevent seizure generation. Identifying how FLNA regulates cellular abnormalities and ultimately epilepsy, perhaps by regulating binding partners and translation is a direction for future studies. Collectively, these data point to a critical role of FLNA in the generation of FCM and epileptic seizures.

Next was examined the small molecule PTI-125, which has been reported to bind aberrant FLNA in Alzheimer's disease brain. Similar to Flna shRNA, it was found that PTI-125 ameliorated neuronal dysmorphogenesis, including increased soma size and dendritic complexity in mice treated from P8 to P28. PTI-125 treatment after P8 did not rescue neuronal placement, which is normally complete by P8. This finding suggests that the environment is not permissive for later migration and/or that once neurons have entered dendritic development (>P8), migration cannot be reinitiated. Mice treated with PTI-125 starting during the neonatal period displayed reduced seizure frequency compared to littermate mice treated with vehicle (saline) during the same period. The fact that neuronal misplacement was not rescued whereas seizure activity was decreased by PTI-125 is in agreement with a previous report that misplacement is not required for seizure activity. This finding also shows that alleviating seizure activity can be achieved even if neuronal misplacement is not rescued. Considering that most patients with epilepsy would be treated after the onset of seizures, also examined were the effects of PTI-125 on seizures after mice had experienced seizures for one week or for more than a month. Convulsive seizures are visible at three weeks of age. Treatment of juvenile mice with PTI-125 at 29 (about one week after seizure onset) partially normalized soma size and dendritic abnormalities, and reduced seizure frequency (by 67%). Mice treated with PTI-125 starting at P61 (>one month after seizure onset) and recorded prior to and during treatment exhibited a progressive decrease in seizure frequency over time, reaching a 60% decrease after 30 days of treatment. By contrast, seizure activity in saline-treated mice increased over time.

In conclusion, targeting FLNA with shRNA gene therapy or the small molecule PTI-125 may offer an alternative option for treating seizures and epilepsy in patients with TSC or selective FCDII without altering mTORC1 activity. These treatment options would likely not be applicable to all patients with FCD, but those with mutations in PI3K-Rheb pathway genes. The proposed treatment would nevertheless be applicable to all TSC individuals. The findings presented here suggest the possibility of combination therapy with mTORC1 blocker, everolimus (a rapamycin derivate), perhaps at lower and less adverse doses. A more thorough study of dosing and duration of treatment might identify a regimen to enhance PTI-125's efficacy in treating seizures. Clinical development of PTI-125 for another indication (Alzheimer's disease) is already underway, which should greatly facilitate clinical application in patients with TSC and FCDII with mutations in PI3K-Rheb pathway genes.

Example 6

Overview: KGN efficacy on neuron morphology and seizure activity using video-EEG recordings will be tested. Two different doses of KGN on seizure activity will be tested. The doses to be tested will be determined by ore-testing the effect of different KGN doses on neuronal morphology.

Research Design

For morphology: mice expressing $Rheb^{CA}$ in the medial prefrontal cortex (mPFC) will be generated. Mice will be treated with KGN at different doses from P8 to P28. Then neuronal soma size and dendritic complexity and length will be analyzed at P28.

For seizures: Mice expressing $Rheb^{CA}$ in the medial prefrontal cortex (mPFC) that have convulsive seizures will also be generated. A 2-3 µg/µl concentration of $Rheb^{CA}$ that was used for data in FIGS. 3E-3G will be used. Mice will be pre-screened for seizure activity by visual observation. seizures will be routinely observe by 21 days of age. Mice will then undergo EEG recording and video-monitoring 24/7 starting at 6-8 weeks.

Experiment 1: Mice will be randomly split into two groups: one that receives vehicle and another one that receives KGN used at the dose that was the most efficient at rescuing neuronal morphology. KGN will be given from P28 for 4 weeks. Seizure activity will be recorded for the last week. Based on past experience and power analysis, aprroximately 15-20 mice will be needed to reach a significant 50% effect size.

Experiment 2: Mice will be recorded for 6 weeks. Mice will receive vehicle for the first 2 weeks, followed by KGN injections. Control mice will receive vhecile throughout the recordings. aprroximately 10-15 mice will be needed to reach a significant 50% effect size.

Analysis of KGN efficacy: Several types of analyses will be performed. First a Friedman test will be used followed by Dunn's test. The seizure frequency will also be averaged for the last 2 weeks of recordings and a paired t-test statistical analysis will be performed.

Brain pathology analysis: Soma size post-EEG recordings will be quantified for all the mice studied.

Expected results: It is aniticipated that KGN significantly normalizes neuronal morphology completely or partially and significantly decreases seizure frequency.

TABLE 1

| Information for patients with FCDII | | | | | | | |
|---|---|---|---|---|---|---|---|
| Patient # FCD type | Relative FLNA quantity | Age at surgery (yrs) | Duration of epilepsy history | Gender | Location of surgical resection | Pathology | Antiseizure drugs |
| | | | | Immunostaining | | | |
| 1 FCD IIb | N/A | 2 | 1 year | M | L superior frontal gyrus | Cortical dyslamination, dysmorphic neurons, balloon cells, and gliosis | Topiramate, oxcarbazepine, lev |

TABLE 1-continued

Information for patients with FCDII

| Patient # FCD type | Relative FLNA quantity | Age at surgery (yrs) | Duration of epilepsy history | Gender | Location of surgical resection | Pathology | Antiseizure drugs |
|---|---|---|---|---|---|---|---|
| 2 FCD IIb | N/A | 5 | 3 years | M | R supramarginal gyrus | Cortical dyslamination, dysmorphic neurons, and balloon cells | Oxcarbazepine |
| 3 FCD IIb | N/A | 4 | 2 months | M | L superior and middle frontal gyrus | Cortical dyslamination, dysmorphic neurons, and balloon cells; IHC: NF-Pan+, NeuN+, Syn+, Olig2+, GFAP+, CD34+ | Lev, sodium valproate |
| 4 FCD IIb | N/A | 26 | 6 years | F | R middle frontal gyrus | Cortical dyslamination, dysmorphic neurons, and balloon cells; IHC: NeuN+, GFAP+, Olig2+, CgA+ | Oxcarbazepine, lev, sodium valproate |
| 5 FCD IIa | N/A | 8 | 7 years | F | L superior frontal gyrus | Cortical dyslamination, dysmorphic neurons, and immature neurons; IHC: NeuN+, GFAP+, Olig2+, Ki67 (<1%+), p53−, MGMT−, IDH−, CD34− | Oxcarbazepine, sodium valproate |
| Immunoblotting | | | | | | | |
| 1 FCD IIa | 2.24 | 30 | 5 years | M | L temporal | Cortical dyslamination, dysmorphic neurons, and gliosis | Carbamazepine |
| 2 FCD IIa | 1.38 | 16 | 2 years | M | R occipital | Cortical dyslamination and dysmorphic neurons | Lev, oxcarbazepine |
| 3 FCD IIa | 2.31 | 7 | 7 years | F | R superior and middle frontal gyrus | Cortical dyslamination and dysmorphic neurons | Lev, phenobarbital, sodium valproate, oxcarbazepine, phenytoin, clonazepam, lamotrigine, topiramate |
| 4 FCD IIa | 1.51 | 5 | 3 years | M | L frontal | Cortical dyslamination and dysmorphic neurons; IHC: NF-Pan+, NeuN+, GFAP+, CD34−, CgA+ | Carbamazepine, oxcarbazepine, lev, topiramate, sodium valproate |
| 5 FCD IIa | 2.26 | 9 | 1 month | M | L middle frontal gyrus | Cortical dyslamination, dysmorphic neurons | Phenobarbital, oxcarbazepine |
| 6 FCD IIa | 1.54 | 11 | 3 years | F | R occipital | Cortical dyslamination, dysmorphic neurons | Lev |
| 7 FCD IIb | 1.04 | 15 | 12 years | F | R angular gyrus and supramarginal gyrus | Cortical dyslamination, dysmorphic neurons, balloon cells, and gliosis | Carbamazepine, topiramate |
| 8 FCD IIa | 0.97 | 12 | 8 years | M | L insular lobe | Cortical dyslamination and dysmorphic neurons | Lamotrigine, topiramate |
| 9 FCD IIb | 0.57 | 26 | 14 years | F | R orbitofrontal gyrus and gyrus rectus | Cortical dyslamination, dysmorphic neurons, and balloon cells; IHC: NeuN+, GFAP+, CgA+, Olig2+, Ki67− | Magnesium valproate, lev, phenobarbital sodium bromide, anti-triazine |

TABLE 1-continued

Information for patients with FCDII

| Patient # FCD type | Relative FLNA quantity | Age at surgery (yrs) | Duration of epilepsy history | Gender | Location of surgical resection | Pathology | Antiseizure drugs |
|---|---|---|---|---|---|---|---|
| 10 FCD IIb | 1.76 | 29 | 6 years | M | L frontal and cingulate gyrus | Cortical dyslamination, dysmorphic neurons, balloon cells and immature neurons. | Sodium valproate, carbamazepine |
| 11 FCD IIb | 1.97 | 10 | 1 year | M | L frontal | Cortical dyslamination, dysmorphic neurons, balloon cells, and gliosis | Oxcarbazepine |
| 12 FCD IIb | 2.09 | 11 | 10 years | M | R temporal, amygdala, hippocampus | Cortical dyslamination, dysmorphic neurons, and balloon cells. | Carbamazepine |

TABLE 2

Information for control patients

| Age at surgery (yrs) | Relative FLNA quantity | Gender | Location of resection | Causes | Surgical Diagnosis |
|---|---|---|---|---|---|
| 13 | 0.417 | F | Right (R) temporal | Fall from height | R temporal brain contusion |
| 13 | 0.73 | M | R occipital | Fall from height | R occipital brain contusion |
| 16 | 1.71 | M | Left (L) occipital | Fall from height | L occipital brain contusion, Subdural hemorrhage, basilar skull fracture |
| 5 | 1.31 | M | L frontal | Car accident | L frontal brain contusion, diffuse axonal injury, frontal bone fracture |
| 9 | 1.78 | M | R occipital | Car accident | R occipital brain contusion, occipital bone fracture |
| 6 | 0.87 | M | R frontal | Fall from height | R frontal brain contusion, subarachnoid hemorrhage, frontal bone fracture |
| 23 | 0.52 | M | R parietal | Fall from height | R parietal Brain contusion, parietal bone fracture |
| 27 | 0.27 | F | Bifrontal | Car accident | Bifrontal Brain contusion, bifrontal bone fracture, L temporal bone fracture |
| 10 | 1.11 | M | R frontal | Fall from height | R frontal brain contusion, epidural hemorrhage, subarachnoid hemorrhage |
| 11 | 1.06 | F | L frontal | Car accident | L frontal brain contusion, subarachnoid hemorrhage, frontal bone fracture |
| 15 | 1.22 | M | R temporal | Car accident | R frontal brain contusion, subarachnoid hemorrhage, diffuse axonal injury |

None of the patients had a history of drug.

TABLE 3

Summary of statistical tests

| Fig. | Tests | Statistical values | P values | n | Definition of n |
|---|---|---|---|---|---|
| 1G | Student's t-test, unpaired, two-tailed | t = 7.007 df = 99 | <0.0001 | 15 control and 19 SMI-311+ | Number of cells from 3 human samples |
| 1I | Student's t-test, unpaired, two-tailed | t = 3.121 df = 22 | 0.005 | 12 | Number of human samples per condition |
| 2B | One way ANOVA with Tukey post-test | F (3, 8) = 46.84 | <0.0001 | 3 | Number of neuronal culture sets per condition |

TABLE 3-continued

Summary of statistical tests

| Fig. | Tests | Statistical values | P values | n | Definition of n |
|---|---|---|---|---|---|
| 2C | One way ANOVA with Tukey post-test | $F(3, 8) = 73.46$ | <0.0001 | 3 | Number of neuronal culture sets per condition |
| 2F | Student's t-test, paired, two-tailed | $t = 25.6\ df = 34$ | <0.0001 | 35 | Number of cells in 4 mice per condition |
| 2G | Student's t-test, paired, two-tailed | $t = 3.058\ df = 4$ | 0.0377 | 5 | Number of cortices |
| 3A | One way ANOVA with Tukey post-test | $F(2, 98) = 682.5$ | 0.0001 | 30/35/36 | Number of slices in 6 mice per condition (GFP/Rheb$^{CA}$ + Luc shRNA/Rheb$^{CA}$ + Flna shRNA) |
| 3B | One way ANOVA with Tukey post-test | $F(2, 132) = 356.5$ | <0.0001 | 45 | Number of cells per condition (3 slices/mouse, 3 mice) |
| 3C | Two-way repeated measures ANOVA Bonferroni post-test | Interaction: $F(40, 1380) = 10.31$, $p < 0.0001$ Row factor: $F(20, 1380) = 294.9$, $p < 0.0001$ Column factor: $F(2, 69) = 18.58$, $p = 0.0219$ Subjects (matching) $F(69, 1380) = 10.78$, $p < 0.0001$ | 0.05 | 25-21-26 | Number of cells in 3 mice per condition (GFP-Rheb$^{CA}$ + Luc shRNA-Rheb$^{CA}$ + Flna shRNA) (3 slices per mouse) |
| 3D | One way ANOVA with Tukey post-test | $F(2, 68) = 27.29$ | <0.0001 | 25-21-26 | Number of cells in 4 mice per condition (GFP-Rheb$^{CA}$ + LMc shRNA- Rheb$^{CA}$ + Flna shRNA) (3 slices per mouse) |
| 3G | Mann Whitney U test, two-tailed | $U = 2$ | <0.0001 | 11-10 | Number of mice per condition (Rheb$^{CA}$ + Luc shRNA - Rheb$^{CA}$ + Flna shRNA) |
| 3H | Student's t-test, unpaired, two-tailed | $t = 0.2668\ df = 58$ | 0.7905 | 30 | Number of cell doublets (ratio GFP+/GFP−) in 4 mice per condition |
| 4B | One way ANOVA with Tukey post-test | $F(3, 181) = 75.52$ | <0.0001 | 46 | Number of cells in 4 mice per condition |
| 4D, left | Two-way repeated measures ANOVA Bonferroni post-test | Rheb$^{CA}$ + vehicle vs Rheb$^{CA}$ + PTI-125 Interaction: $F(30, 2400) = 20.5$, $p < 0.0001$ Row factor: $F(30, 2400) = 446.4$, $p < 0.0001$ Column factor: $F(1, 80) = 45.3$, $p = 0.0219$ Subjects (matching) $F(80, 2400) = 11.91$, $p < 0.0001$ Rheb$^{CA}$ + vehicle vs Rheb$^{CA}$ + PTI-125 Interaction: $F(30, 1950) = 23.12$, $p < 0.0001$ Row factor: $F(30, 1950) = 401.5$, $p < 0.0001$ Column factor: $F(1, 65) = 58.75$, $p = 0.0219$ | 0.05 0.05 | 47-35 47-31 | Number of cells in 6 mice per condition (vehicle vs PTI-125) |

TABLE 3-continued

Summary of statistical tests

| Fig. | Tests | Statistical values | P values | n | Definition of n |
|---|---|---|---|---|---|
| | | Subjects (matching) $F (65, 1950) = 8.781$, $p < 0.0001$ | | | |
| 4D, right | One way ANOVA with Tukey post-test | $F (3, 139) = 58.05$ | <0.0001 | 32-47-31-35 | Number of cells in 6 mice per condition (GFP + vehicle- $Rheb^{CA}$ + vehicle- $Rheb^{CA}$ + 6mg/kg PTI-125- $Rheb^{CA}$ + 12 mg/kg PTI-125 |
| 4E | Student's t-test, unpaired, two-tailed | $t = 0.4713$ $df = 12$ | 0.6459 | 6 | Number of cortices per condition |
| 4G | Mann Whitney U test, two-tailed | $U = 1$ | 0.0031 | 5-8 | Number of mice per condition ($Rheb^{CA}$ + vehicle - $Rheb^{CA}$ + PTI-125) |
| 4H | Student's t-test, unpaired, two-tailed | $t = 0.5367$ $df = 7$ | 0.6081 | 4-5 | Number of mice per condition ($Rheb^{CA}$ + vehicle - $Rheb^{CA}$ + PTI-125) |
| 4I | Student's t-test, unpaired, two-tailed | $t = 0.7904$ $df = 28$ | 0.4359 | 15 | Number of cells in 5 mice per condition ($Rheb^{CA}$ + vehicle - $Rheb^{CA}$ + PTI-125) |
| 4J | Student's t-test, unpaired, two-tailed | $t = 0.3808$ $df = 58$ | 0.7047 | 30 | Number of cells in 5 mice per condition ($Rheb^{CA}$ + vehicle - $Rheb^{CA}$ + PTI-125) |
| 5D | Two-way repeated measures ANOVA Sidak post-test | $Rheb^{CA}$ + vehicle vs $Rheb^{CA}$ + PTI-125 Interaction: $F (30, 2400) = 20.5$, $p < 0.0001$ Row factor: $F (30, 2400) = 446.4$, $p < 0.0001$ Column factor: $F (1, 80) = 45.3$, $p = 0.0219$ Subjects (matching) $F (80, 2400) = 11.91$, $p < 0.0001$ | 0.05 | 21 | Number of cells in 4 mice per condition ($Rheb^{CA}$ + vehicle - $Rheb^{CA}$ + PTI-125) |
| 5E | One way ANOVA with Tukey post-test | $F (2, 60) = 53.15$ | <0.0001 | 21 | Number of cells in 4 mice per condition (GFP + vehicle - $Rheb^{CA}$ + vehicle - $Rheb^{CA}$ + PTI-125) |
| 5G | Mann Whitney U test, two-tailed | $U = 60.5$ | 0.0158 | 15-16 | Number of mice per condition ($Rheb^{CA}$ + vehicle - $Rheb^{CA}$ + PTI-125) |
| 5J | One way ANOVA with Tukey post-test | $F (3, 26) = 5.634$ | 0.0041 | 7 (vehicle) 8 (vehicle to PTI-125) | Number of mice per condition |
| 5K | Wilcoxon test, two-tailed | | 0.0156 | 7 | Number of mice receiving vehicle and then PTI-125 |
| 6A | Fisher's exact test, two-sided | | 0.0343 | 3/29 (vehicle) 11/32 (PTI-125) | Number of mice without/with seizures per condition |
| 6C | Mann Whitney U test, two-tailed | $U = 166.5$ | <0.0001 | 27-32 | Number of mice per condition ($Rheb^{CA}$ + vehicle - $Rheb^{CA}$ + PTI-125) |
| S1E | Mann Whitney U test, two-tailed | $U = 111$ | <0.0001 | 125 | Number of cells per condition from 5 human samples, |

TABLE 3-continued

Summary of statistical tests

| Fig. | Tests | Statistical values | P values | n | Definition of n |
|---|---|---|---|---|---|
| S1F | Student's t-test, unpaired, two-tailed | t = 27.37 df = 248 | <0.0001 | 125 | 25 cells per samples from 5 randomly selected area of interest Number of cells per condition from 5 human samples, 25 cells per samples from 5 randomly selected area of interest |
| S4A | Student's t-test, unpaired, two-tailed | t = 0.7576 df = 10 | 0.4662 | 7 and 5 | Number of FCDIIa and FCDIIb |
| S4B | Pearson correlation | $R^2$ = 0.03607 | 0.5544 | 12 | Number of FCDII |
| S4C | Pearson correlation | $R^2$ = 0.301 | 0.0647 | 12 | Number of FCDII |
| S5B up | Student's t-test, unpaired, two-tailed | t = 12.02 df = 10 | <0.0001 | 6 | Number of cultures per condition |
| S5B below | Student's t-test, unpaired, two-tailed | t = 0.6001 df = 10 | 0.5618 | 6 | Number of cultures per condition |

TABLE 4

Plasmids

| | IUE concentration | Notes/Origin |
|---|---|---|
| pCAGGS-Rheb S16H (i.e., pCAG-Rheb$^{CA}$) | 1.5 µg/µl | National Institute of Infectious Diseases, Tokyo |
| pCAG-tdTomato | 1.5 µg/µl | Addgene (##83029)(19) |
| pCAG-GFP | 1.5 µg/µl | Addgene (#11150) |
| pCALNL-dsRed2 | 1.5 µg/µl | Addgene (#13769) |
| pCAG-Cre | 0.001 µg/µl | Addgene (##13775) |
| pCGLH-Flna shRNA | 1.5 µg/µl | The shRNA sequence for FLNA (5' CCTATGAAGCTGGAACCTATA 3'). |
| pCGLH-Luciferase shRNA | 1.5 µg/µl | 5' CGCTGAGTACTTCGAAATGTC 3', sequence from clone #TRCN0000072259 |
| pcDNA3-FLAG-MTOR-L1460P | 1 µg/µl | Addgene (#69006) |
| pcDNA3-FLAG-MTOR-S2215Y | 1 µg/µl | Addgene (#69013) |
| pcDNA3-EGFP | 1 µg/µl | Addgene (#13031) |

TABLE 5

Primary and Secondary antibodies

| Antibody | Company | Catalog Number | Host animal | Concentration used in IHC or immunoblot (IB) or IF |
|---|---|---|---|---|
| Primary | | | | |
| Filamin A (FLNA) for IB and IF | Abcam | ab51217 | Rabbit | 1:5000 (IB)/ 1:500 (IF) |
| Filamin A (FLNA) for IHC | Abcam | ab76289 | Rabbit | 1:500 (IHC) |
| SMI-311 | Covance | SMI-311R | Mouse | 1:250 (IF) |
| Phospho-S6 (S240/244) | Cell Signaling | #5364 | Rabbit | 1:500 (IHC)/ 1:5000 (IB)/ 1:800 (IF) |
| S6 | Cell Signaling | #2217 | Rabbit | 1:5000 (IB) |
| Tubulin | Cell Signaling | #2146 | Rabbit | 1:5000 (IB) |
| ER-81 | Covance | PRB-362C | Rabbit | 1:10,000 (IF) |
| GFP | Aves | GFP-1010 | Chicken | 1:800 (IF) |
| GAPDH | Santa Cruz | sc-25778 | Rabbit | 1:5000 (IB) |
| Rheb | Santa Cruz | sc-6341 | Goat | 1:1000 (IB) |
| ERK1/2 | Santa Cruz | Sc-94 | Rabbit | 1:5000 (IB) |
| DAPI | Life Technologies | D1306 | | 1:5000 |
| Secondary | | | | |
| HRP-conjugated anti-rabbit | Cell signaling | 7074 | Donkey | 1:5000 (IB) |
| HRP-conjugated anti-goat | Thermo Fisher Scientific | A27014 | Rabbit | 1:2000 |
| α Mouse IgG Alexa Fluor 568 | Thermo Fisher Scientific | A-11004 | Goat | 1:1000 |
| α Mouse IgG Alexa Fluor 555 | Thermo Fisher Scientific | A28180 | Goat | 1:1000 |
| α Rabbit IgG Alexa Fluor 555 | Thermo Fisher Scientific | A-31572 | Donkey | 1:1000 |
| α Rabbit IgG Alexa Fluor 488 | Thermo Fisher Scientific | A-11034 | Goat | 1:1000 |
| α Chicken IgG Alexa Fluor 488 | Thermo Fisher Scientific | A-11039 | Goat | 1:1000 |
| α Rabbit IgG Alexa Fluor 647 | Thermo Fisher Scientific | A-31573 | Donkey | 1:1000 |

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of treating epilepsy in a subject in need thereof, the method comprising providing to the subject an effective amount of an FLNA modulator, wherein the epilepsy is intractable epilepsy associated with focal cortical dysplasia (FCD) type II or tuberous sclerosis complex (TSC).

2. The method according to claim 1, wherein the FLNA modulator is PTI-125.

3. The method according to claim 1, wherein the FLNA modulator is formulated in a pharmaceutical composition comprising at least one pharmaceutically acceptable excipient.

4. The method according to claim 1, wherein the subject is a mammal.

5. The method according to claim 1, wherein the subject is a human.

* * * * *